US008634080B2

(12) United States Patent
Bogdanowicz

(10) Patent No.: US 8,634,080 B2
(45) Date of Patent: Jan. 21, 2014

(54) METHOD FOR DETERMINING AN ACTIVE DOPANT CONCENTRATION PROFILE

(71) Applicants: IMEC, Leuven (BE); Katholieke Universiteit Leuven, Leuven (BE)

(72) Inventor: Janusz Bogdanowicz, Liège (BE)

(73) Assignees: IMEC, Leuven (BE); Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 13/744,880

(22) Filed: Jan. 18, 2013

(65) Prior Publication Data

US 2013/0194577 A1 Aug. 1, 2013

Related U.S. Application Data

(63) Continuation of application No. PCT/EP2011/062483, filed on Jul. 20, 2011.

(60) Provisional application No. 61/366,460, filed on Jul. 21, 2010.

(51) Int. Cl.
*G01N 21/55* (2006.01)

(52) U.S. Cl.
USPC .......................................... 356/447; 356/445

(58) Field of Classification Search
USPC ......... 356/128, 445–448, 432–435, 601, 609, 356/369, 72, 492, 493, 496, 498, 502–504, 356/36, 237.1–237.6; 438/350, 447, 7; 250/201.2, 201.1, 559.45, 559.46, 250/559.4, 307, 308, 310
See application file for complete search history.

(56) References Cited

U.S. PATENT DOCUMENTS

| | | | | |
|---|---|---|---|---|
| 6,323,951 | B1 * | 11/2001 | Borden et al. | 356/502 |
| 6,392,756 | B1 * | 5/2002 | Li et al. | 356/632 |
| 7,403,022 | B2 * | 7/2008 | Salnik et al. | 324/754.22 |
| 2005/0036136 | A1 | 2/2005 | Opsal et al. | |
| 2005/0062971 | A1 * | 3/2005 | Salnik et al. | 356/432 |
| 2007/0292976 | A1 | 12/2007 | Clarysse et al. | |
| 2008/0224036 | A1 | 9/2008 | Clarysse et al. | |
| 2010/0002236 | A1 * | 1/2010 | Bogdanowicz | 356/445 |
| 2010/0238449 | A1 * | 9/2010 | Bogdanowicz | 356/445 |

OTHER PUBLICATIONS

Fabian Dortu, Low frequency modulated optical reflectance for the one-dimensional characterization of ultra shallow junctions, May 5, 2009, Ph.D. thesis, Katholieke Universiteit Leuven.*

(Continued)

*Primary Examiner* — Tara S Pajoohi Gomez
*Assistant Examiner* — Michael P LaPage
(74) *Attorney, Agent, or Firm* — Knobbe, Martens, Olson & Bear LLP

(57) ABSTRACT

A method for determining an active dopant concentration profile of a semiconductor substrate based on optical measurements is disclosed. The active dopant concentration profile includes a concentration level and a junction depth. In one aspect, the method includes obtaining a photomodulated optical reflectance (PMOR) amplitude offset curve and a PMOR phase offset curve for the semiconductor substrate based on PMOR measurements, determining a decay length parameter based on a first derivative of the amplitude offset curve, determining a wavelength parameter based on a first derivative of the phase offset curve, and determining, from the decay length parameter and the wavelength parameter, the concentration level and the junction depth of the active dopant concentration profile.

19 Claims, 12 Drawing Sheets

(56) References Cited

OTHER PUBLICATIONS

Bogdanowicz et al., "Advances in optical carrier profiling through high-frequency modulated optical reflectance," Journal of Vacuum Science and Technology, Part B, vol. 26, No. 1. pp. 310-316, 2008.
Bogdanowicz et al., "Electrothermal theory of photomodulated optical reflectance on active doping profiles in silicon," Journal of Applied Physics, vol. 108, No. 10, p. 104908-1-104908-25, 2010.
Bogdanowicz et al., "Nondestructive extraction of junction depths of active doping profiles from photomodulated optical reflectance offset curves," Journal of Vacuum Science and Technology, part B, vol. 28, No. 1, pp. C1C1-C1C7, 2010.
International Preliminary Report on Patentability and Written Opinion issued Jan. 22, 2013 for PCT Application No. PCT/EP2011/062483.
International Search Report mailed Oct. 18, 2011 for PCT Application No. PCT/EP2011/062483.
Nicolaides et al., "Nondestructive analysis of ultrashallow junctions using thermal wave technology," Review of Scientific Instruments, vol. 74, No. 1, 2003.

* cited by examiner

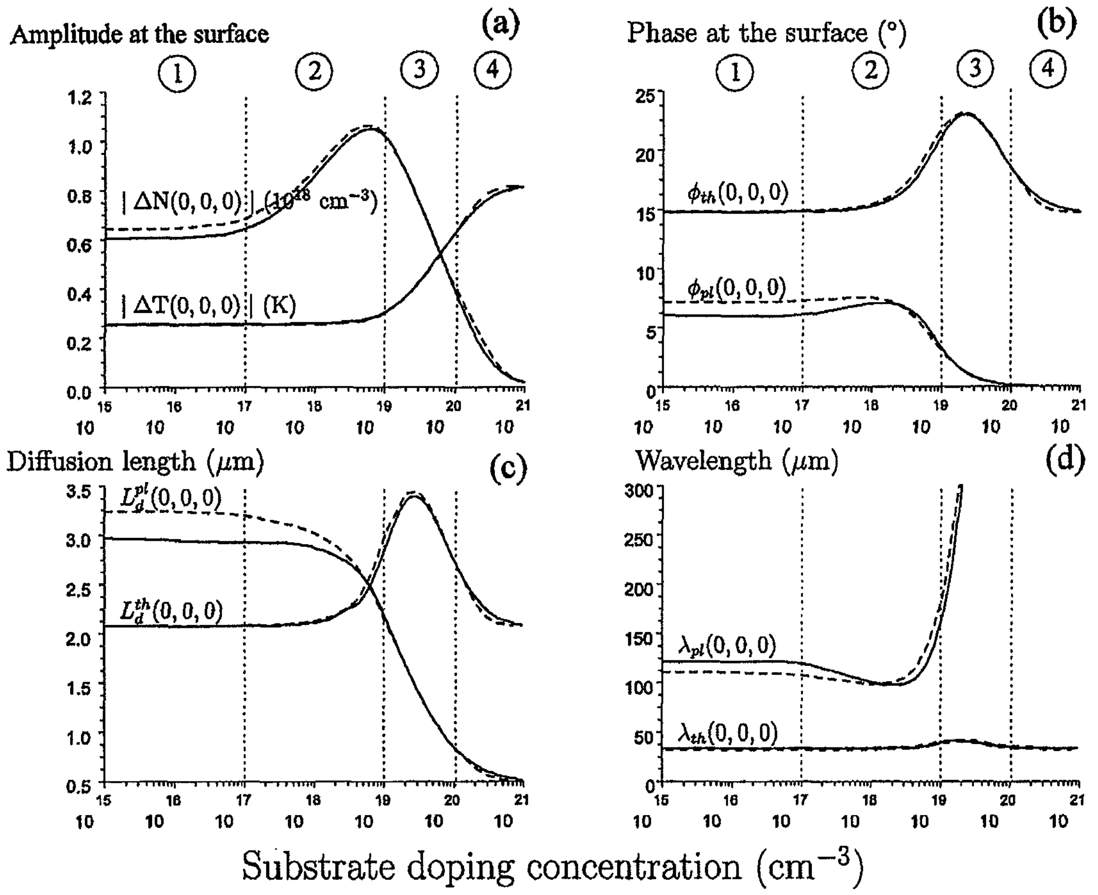

FSEM numerical simulation

Semi-analytical solution

① $i\omega\Delta N = D^*\nabla^2(\Delta N) + G$ $\rho c_p i\omega\Delta T = k_{th}\nabla^2(\Delta T) + G_{th}^{direct}$ ② $i\omega\Delta N = D^*\nabla^2(\Delta N) + G - Rec$ $\rho c_p i\omega\Delta T = k_{th}\nabla^2(\Delta T) + G_{th}^{direct}$ ③ $i\omega\Delta N = D^*\nabla^2(\Delta N) + G - C_p P_0^2 \Delta N$ $\rho c_p i\omega\Delta T = k_{th}\nabla^2(\Delta T) + G_{th}^{direct} + G_{th}^{recombination}$ ④ $0 = G - C_p P_0^2 \Delta N$ $\rho c_p i\omega\Delta T = k_{th}\nabla^2(\Delta T) + G_{th}^{direct} + G_{th}^{recombination}$

FIG. 9

METHOD FOR DETERMINING AN ACTIVE DOPANT CONCENTRATION PROFILE

CROSS REFERENCE TO RELATED APPLICATIONS

This application is a continuation of PCT Application No. PCT/EP2011/062483, filed Jul. 20, 2011, which claims priority under 35 U.S.C. §119(e) to U.S. provisional patent application 61/366,460 filed on Jul. 21, 2010. Each of the above applications is incorporated herein by reference in its entirety.

BACKGROUND OF THE INVENTION

1. Field of the Invention

The disclosed technology relates to the field of optical measurements for determining an active dopant profile, and more particularly, to an optical measurement method and system for determining the peak concentration and junction depth of an active dopant profile.

2. Description of the Related Technology

The electrical characterization of the source and drain extension regions of CMOS transistors is highlighted in the ITRS roadmap for semiconductors as a major challenge for future technology nodes. In practice, there is a clear need for techniques which are simultaneously accurate, non-destructive, fast, local and highly reproducible. The photomodulated optical reflectance (PMOR) technique has shown to be a very promising candidate to solve this need.

The photomodulated optical reflectance (PMOR) is a fast, non-contact technique. It has shown very promising to solve the need for non-destructive carrier profiling tool for ultra-shallow junctions (USJs). This pump-probe technique is based on the measurement by a probe laser of the reflectance change due to the modulated pump laser-induced changes in refractive index. The theoretical basis of the technique has been widely studied on metals, homogeneous semiconducting materials and as-implanted (i.e. damaged) silicon samples. The existing theories are all based on simplified optical and transport models, where a certain number of effects are neglected without any justification. Typically, the optical model is based on the Drude electrorefractive effect and the thermorefractive effect. As for the transport models, they usually only consider diffusion and recombination effects. This assumes that, apart from thermal carrier generation and recombination heat, no coupling exists between the carrier and heat transport equations.

Thus, although the PMOR technique has been widely studied on homogeneous bulk material and on as-implanted (i.e. unannealed) doping profiles, the extension towards active doping profiles allows for further improved methods and systems for determining active dopant profiles.

SUMMARY OF CERTAIN INVENTIVE ASPECTS

Certain inventive aspects relate to good methods for determining an active dopant profile in a semiconductor substrate. It is an advantage of one inventive aspect that accurate determination of the peak doping concentration and/or junction depth can be obtained. It is an advantage of one inventive aspect that a method and/or system is provided for independently extracting the peak dopant concentration and junction depth in a semiconductor substrate from a single measurement.

The method and/or system may be, amongst others, suitable for determining the active dopant profile in semiconductor layers having highly-lowly doped structures, i.e. structures having a dopant or carrier concentration profile which shows a maximum near the surface and is decreasing towards the bulk of the substrate, such as for example semiconductor layers formed and/or doped by CVD, implantation, or diffusion. Such highly-lowly doped structures may be considered as structures having a carrier profile that has a maximum near the surface and decreases towards the substrate.

It is an advantage of one inventive aspect to provide a method or system to extract the junction depth with sub-nm reproducibility for depths below about 45 nm, particularly for depths ranging from about 15 to 30 nm.

It is an advantage of one inventive aspect to provide a method or system to extract the peak doping concentration of a doping profile.

It is an advantage of one inventive aspect that a complete active doping profile can be measured for samples having a high doping concentration without substantially destroying the samples.

It is an advantage of one inventive aspect that carrier profiles in ultra shallow junctions can be determined non-destructively, i.e. without sample preparation.

It is an advantage of one inventive aspect that doping incorporation may be monitored at key points in the process flow and thus leading to an enhanced product quality.

It is an advantage of one inventive aspect that a method for determining the active dopant profile may be applied in-line, i.e. in the production process environment.

It is an advantage of one inventive aspect that a user friendly and easy to operate method may be applied for determining the active dopant profile of a semiconductor substrate in a short measurement time.

It is an advantage of one inventive aspect that a complete active doping profile can be determined or reconstructed from an optical measurement on the doping profile. The active doping profile may be any arbitrary doping profile.

It is an advantage of one inventive aspect that a unique solution may be determined for the active doping profile based on an optical measurement of the active doping profile.

It is an advantage of one inventive aspect that an unknown arbitrary doping profile may be reconstructed from an optical measurement in a fast and flexible way while no prior assumptions need to be made about the doping concentration or the junction depth.

It is an advantage of one inventive aspect that accurate determination of the doping concentration and/or the junction depth can be obtained, by taking into consideration the effects of local electric fields in the semiconductor substrate, such as the built-in electric field at the junction between two semiconducting regions with different doping concentrations. It is an advantage of one inventive aspect that the respective impacts of the electric field, bandgap-narrowing (BGN) and band-filling on the complex dielectric constant can be taken into account. It is an advantage of one inventive aspect that thermoelectric effects can be taken into account.

One inventive aspect relates to a method for determining an active dopant concentration profile of a semiconductor substrate based on optical measurements, the active dopant concentration profile comprising a concentration level and a junction depth, the method comprising obtaining a photomodulated reflectance (PMOR) amplitude offset curve and a photomodulated reflectance (PMOR) phase offset curve for the semiconductor substrate based on photomodulated reflectance (PMOR) measurements, determining a decay length parameter based on a first derivative of the amplitude offset curve and determining a wavelength parameter based on a first derivative of the phase offset curve, and determining from the decay length parameter and from the wavelength parameter, the concentration level and the junction depth of the active dopant concentration profile.

It was surprisingly found that using the derivative of the amplitude offset curve and the phase offset curve, accurate values of the peak concentration level and the junction depth can be obtained, e.g. taking into account a predetermined dopant profile shape.

The amplitude offset curve may be the offset curve of the normalized amplitude.

Obtaining a PMOR amplitude offset curve and a PMOR phase offset curve for the semiconductor substrate may comprise obtaining a semiconductor substrate having an active dopant concentration profile characterized by a concentration level and a junction depth, and optically measuring a PMOR amplitude offset curve and a PMOR phase offset curve for the obtained semiconductor substrate.

Determining a decay length parameter based on the first derivative of the amplitude offset curve may comprise, for a box-like active dopant profile shape, determining the signal decay length $L^{d}_{signal}$ as $$L_d^{signal} = -\frac{|TP|}{\frac{\partial |TP|}{\partial x}}.$$

$L^{d}_{signal}$ is the lateral distance, i.e. separation between pump laser and probe laser, needed for the amplitude to drop by a factor exp(1). This is linked to a first derivative of the offset curve of the amplitude, e.g. to the slope of the amplitude offset curve.

Determining a wavelength parameter based on the first derivative of the phase offset curve may comprise, for a box-like active dopant profile shape, determining the lateral distance $\lambda_{signal}$ as $$\lambda_{signal} = -2i\pi\frac{TP/|TP|}{\frac{\partial TP/|TP|}{\partial x}}.$$

$\lambda_{signal}$ is the lateral distance, i.e. separation between pump laser and probe laser, needed for the phase to turn 360 degrees. This is linked to a first derivate of the offset curve of the phase, e.g. to the slope of the phase offset curve.

The first derivative of the amplitude offset curve and the first derivative of the phase offset curve are representative for a change of the obtained PMOR amplitude and phase respectively, with the separation between a point of incidence of a pump laser beam and a probe laser beam used for determining the PMOR amplitude and phase.

If thus an (unknown) active dopant profile characterized by an (unknown) junction dept Xj and an (unknown) peak concentration $N_{act}$ is measured using PMOR and the PMOR offset curves (both amplitude and phase) are determined according to one inventive aspect, this will result in 1 PMOR amplitude offset curve and 1 PMOR phase offset curve. By determining the slope of each of these curves, one can determine the lateral decay length value and the wavelength value (corresponding with one experimental data point).

Determining from the decay length parameter and from the wavelength parameter, the concentration level and the junction depth of the active dopant concentration profile may comprise selecting a predetermined concentration profile shape being function of the concentration level and the junction depth, and determining the concentration level and the junction depth of the active dopant concentration profile based on the combination of the predetermined concentration profile shape and the determined decay length parameter and the wavelength parameter.

Selecting a predetermined profile shape may comprise selecting any of a box-like concentration profile shape or a Gaussian concentration profile shape, a Lorentzian shape, a complementary error function or part thereof.

Determining from the decay length parameter and from the wavelength parameter, the concentration level and the junction depth of the active dopant concentration profile may comprise solving the formulas for the signal decay length and for the wavelength taking into account the predetermined concentration profile shape resulting in two equations with two unknowns being the junction depth and the peak concentration level.

For example, when using a box-like active dopant profile, the offset curve TP(x) can be modeled as the optical measurement signal as a function of the pump-probe beam distance separation x, given by:

$$TP(x) = G_{TP}\exp(-i\theta_{TP})\frac{4}{(n_0^2-1)}\cdot$$

$$\left[-\beta\left(\frac{1}{m_e}+\frac{1}{m_h}\right)\left(\underbrace{\frac{|\Delta N_{sub}|^2}{N_{act}}(1-\cos(4\pi n_0 X_j/\lambda_{probe}))\exp\left(-\frac{2x}{L_d^{pl}}\right)}_{layer-plasma}+\right.\right.$$

$$\left.\underbrace{|\Delta N_{sub}|\cos(4\pi n_0 X_j/\lambda_{probe})\exp\left(-\frac{x}{L_d^{pl}}\right)}_{substrate-plasma}\right)\exp(-i\varphi_{pl})$$

$$\left.\exp\left(-\frac{2i\pi x}{\lambda_{pl}}\right)+\underbrace{\delta|\Delta T_{surface}|\exp\left(\frac{-x}{L_d^{th}}\right)\exp(-i\varphi_{th})\exp\left(\frac{-2i\pi x}{\lambda_{th}}\right)}_{thermal}\right]$$

With $G_{TP}$, the thermal probe carrier generation rate, $n_0$ the refractive index, $\Delta N_{sub}$ the excess free electron concentration due to optical injection in the substrate, $N_{act}$ the peak concentration, $X_j$ the junction depth, $\lambda_{probe}$ the wavelength of the probe laser, $L_d^{pl}$ the carrier diffusion length, $\phi_{pl}$ the phase of the plasma wave and $\lambda_{pl}$ the plasma wave wavelength, $L_d^{th}$ the thermal diffusion length, $\phi_{th}$ the phase of the thermal wave and $\lambda_{th}$ the thermal wave wavelength and $\Delta T_{surface}$ the temperature variation at the surface.

Determining from the decay length parameter and from the wavelength parameter, the concentration level and the junction depth of the active dopant concentration profile may comprise correlating the determined decay length parameter and the determined wavelength parameter with known lateral decay length parameter values and known wavelength parameter values determined for well-known active dopant profiles, and determining the concentration level and the junction depth from the correlating.

Correlating and determining therefrom the concentration level and the junction depth may comprise comparing the decay length parameter and the wavelength parameter for the semiconductor substrate with a look up table or a graphical representation of a set of known lateral decay length parameter values and known wavelength parameter values corresponding with known junction depth and peak dopant concentration level.

The method may comprise generating a set of amplitude and phase offset curves for a set of known active dopant concentration profiles, each known active dopant concentration profile being characterized by a different concentration level and/or a junction depth, extracting from the set of generated amplitude and phase offset curves decay length curves, using the first derivative of the amplitude offset curve, and wavelength curves using the first derivative of the phase offset curve, and determining the unknown concentration level and the junction depth by plotting the measured decay length and the wavelength obtained on the unknown sample on the set of extracted decay length curves and wavelength curves respectively.

The known lateral decay length parameter values and the known wavelength parameter values may be obtained by optically measuring (experimentally) semiconductor substrates with a known active dopant profile with known junction depth and known peak dopant concentration level.

The known lateral decay length parameter values and the known wavelength parameter values may be obtained by simulation of semiconductor substrates with a known active dopant profile with known junction depth and known peak dopant concentration level and using a predetermined concentration profile shape. The simulation may be based on a model. It may be based on analytical formulas.

One inventive aspect relates to a computing device for determining an active dopant concentration profile of a semiconductor substrate based on optical measurements, the active dopant concentration profile comprising a concentration level and a junction depth, the computer device comprising an input means configured for obtaining a photomodulated reflectance (PMOR) amplitude offset curve and a photomodulated reflectance (PMOR) phase offset curve for the semiconductor substrate based on photomodulated reflectance (PMOR) measurements, and a processor configured for determining a decay length parameter based on a first derivative of the amplitude offset curve, for determining a wavelength parameter based on a first derivative of the phase offset curve, and for determining from the decay length parameter and from the wavelength parameter, the concentration level and the junction depth of the active dopant concentration profile.

The computing device may be a part of a photomodulated reflectance optical measurement setup or being configured for performing a method as described above.

Another inventive aspect relates to a system for performing photomodulated reflectance, the system comprising a PMOR measurement system comprising a pump laser and a probe laser for obtaining photomodulated reflectance (PMOR) offset curve measurement data and a processing system for receiving photomodulated reflectance (PMOR) offset curve measurement data and for determining a decay length parameter based on a first derivative of the amplitude offset curve, for determining a wavelength parameter based on a first derivative of the phase offset curve, and for determining from the decay length parameter and from the wavelength parameter, the concentration level and the junction depth of the active dopant concentration profile. The system may for example comprise a computing device as described above.

Another inventive aspect relates to a computer program product comprising executable machine readable computer code for, when executed on the computer program product, performing a method as described above.

Another inventive aspect relates to a machine readable data carrier storing such a computer program product or to the transmission of signals representing the computer program product as described above over a local or wide area telecommunications network.

Another inventive aspect relates to a dataset comprising a set of lateral decay length parameter values and wavelength parameter values as function of peak concentration level and a junction depth, each lateral decay length parameter value and wavelength parameter value being based on a first derivative of an amplitude offset curve and a first derivative of a phase offset curve respectively of a photomodulated reflectance measurement of a semiconductor substrate having an active dopant concentration profile having the corresponding peak concentration level and the corresponding junction depth, the dataset being implemented as look up table or graphical representation.

Certain inventive aspects are set out in the accompanying independent and dependent claims. Features from the dependent claims may be combined with features of the independent claims and with features of other dependent claims as appropriate and not merely as explicitly set out in the claims.

These inventive aspects will be apparent from and elucidated with reference to the embodiment(s) described hereinafter.

FIG. **4*a*** illustrates a schematic overview of the band structure of Si, indicating the impact of BGN and BF effects, which may contribute in PMOR and can be taking into account, according to an embodiment of the present invention.

FIG. **4*b*** illustrates the impact of BGN on the variation in the band-to-band absorption coefficient $\alpha_{BTB}$, which may contribute in PMOR and can be taking into account, according to an embodiment of the present invention.

Figure 5:
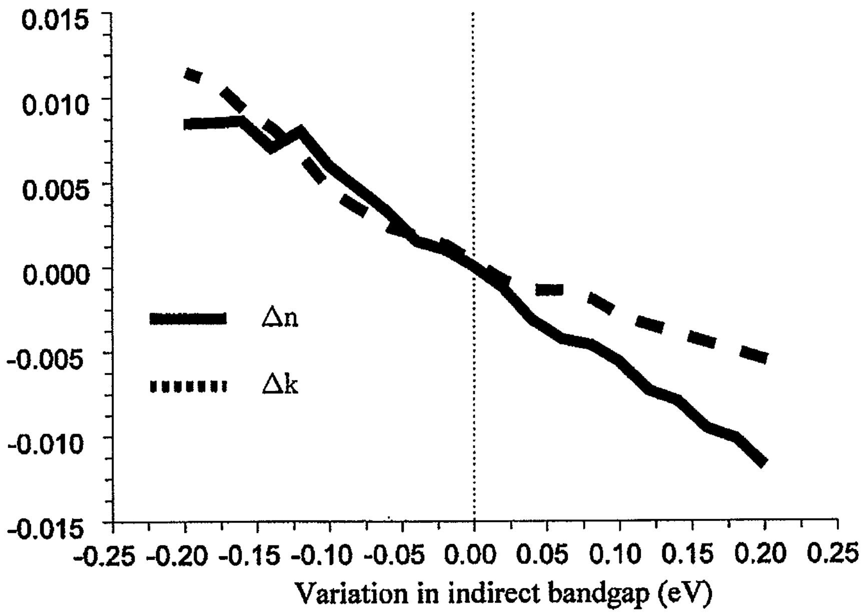

FIG. 5 illustrates variations in the optical functions of silicon at 1.85 eV due to a positive or negative rigid shift in the indirect bandgap, whereby bandgap narrowing corresponds to the left-hand side of the figure (negative variation in indirect bandgap), as can be taking into account in an embodiment of the present invention.

Figure 6:
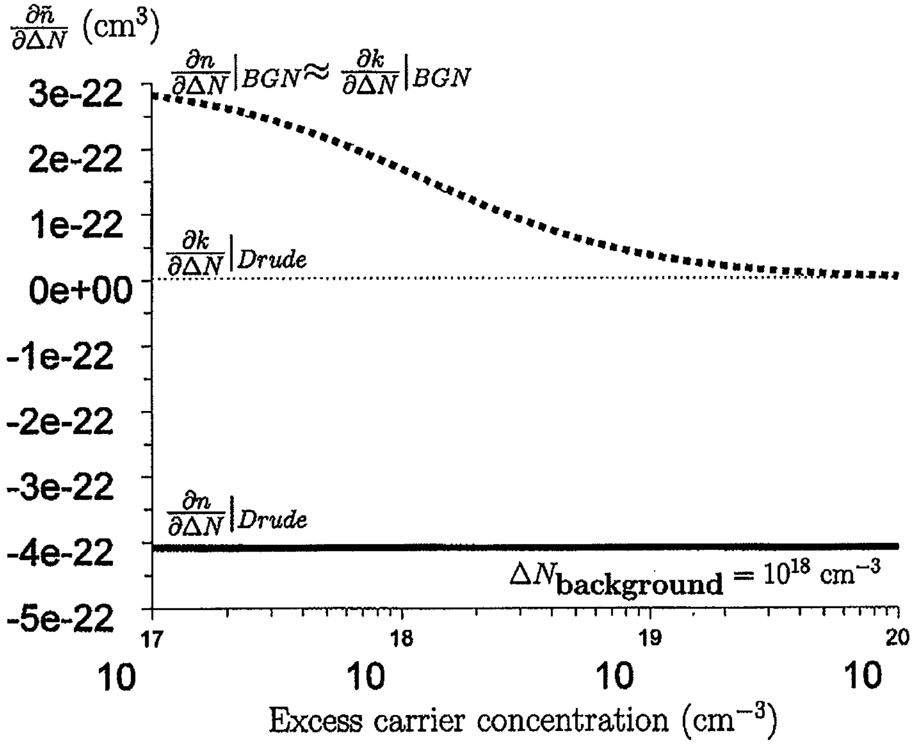

FIG. 6 illustrates the calculated derivative of the real and imaginary refractive indices with respect to free carrier concentration and allows for a comparison between the Drude contribution [formulas (5) and (6)] and the BGN contribution [$\partial\tilde{n}/\partial\Delta N|_{BGN}=0.05(1+i)\partial Eg/\partial\Delta N$] at 1.85 eV photon energy with a $10^{18}$ $cm^{-3}$ background free carrier concentration.

Figure 7:
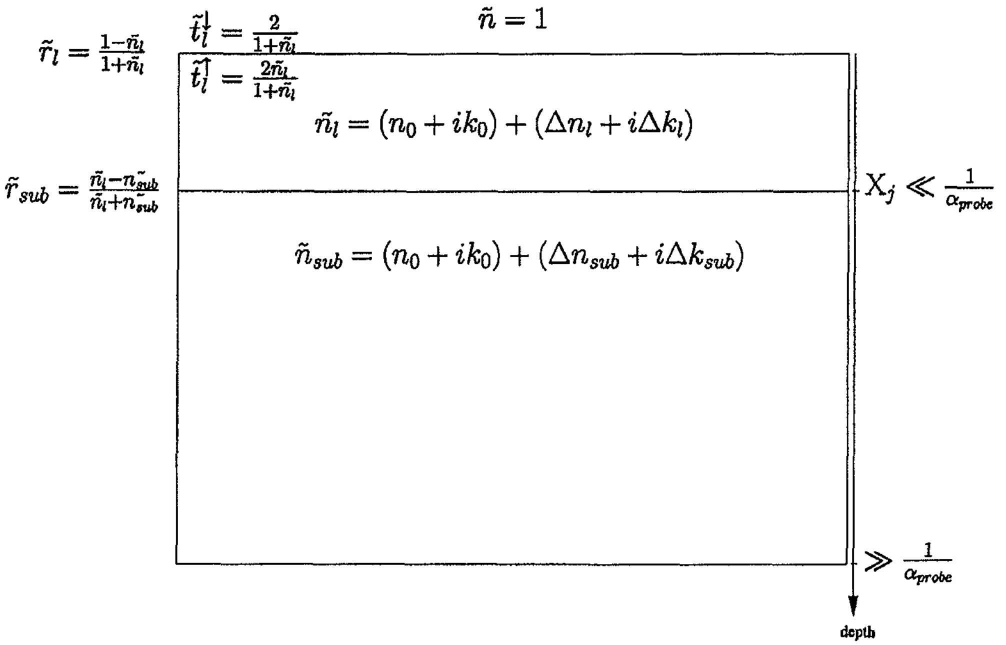

FIG. 7 illustrates a box-like modulated refractive index profile showing two abrupt variations, respectively at the surface and at the interface, as is used in some experimental results, according to one embodiment.

Figure 8:
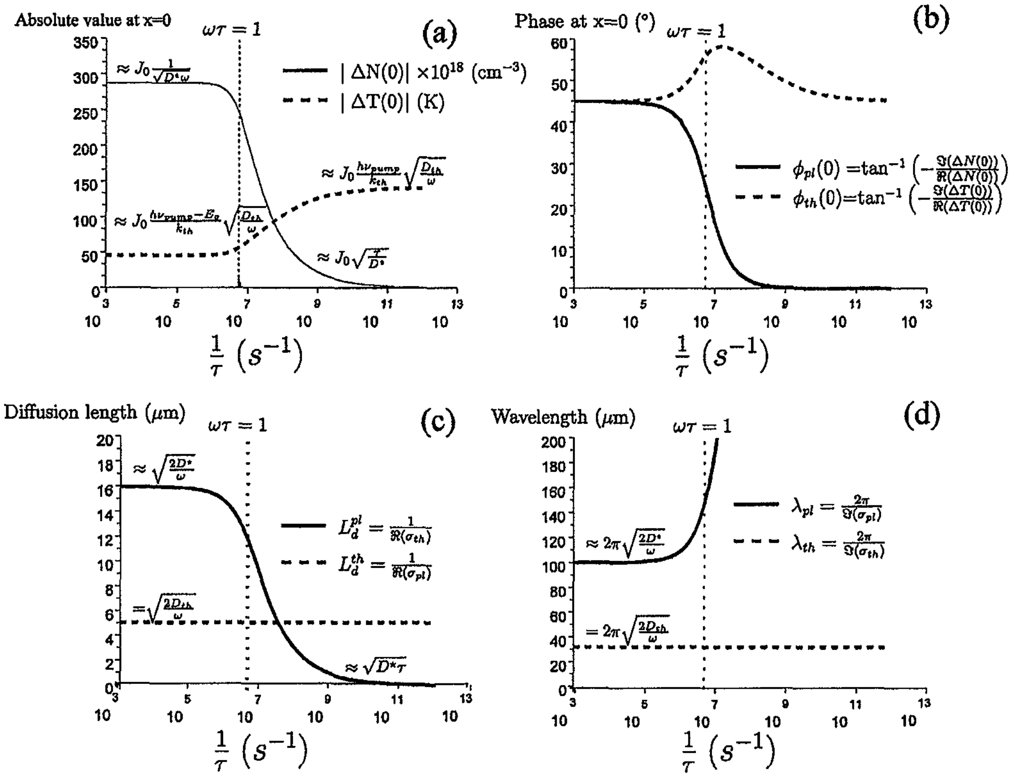

FIG. 8 illustrates variation with recombination lifetime in the one-dimensional plasma (full lines) and thermal (dashed lines) waves, solutions of equations [34] in the case of a TP pump laser. The amplitudes (a) and phases (b) under the beam as well as the lateral diffusion lengths (c) and lateral wavelengths (d) are derived from the analytical solutions expressed in formulas [37]. Asymptotic behaviors are also shown for each curve. The vertical line corresponds to $\omega\tau=1$, i.e. the limit between the diffusion-limited regime (left, long lifetime) and the recombination-limited regime (right, short lifetime).

FIG. 9 illustrates variation with doping in the three-dimensional plasma and thermal waves, solutions of equations [34], in the case of a TP pump laser. The surface amplitudes (a) and phases (b) under the beam as well as the lateral diffusion lengths (c) and laterals wavelengths (d) are derived from a semi-analytical solution (dashed lines) and a numerical solution (full lines). Four regions can be identified, the corresponding simplified equations of which are shown on the right-hand side.

Figure 10:
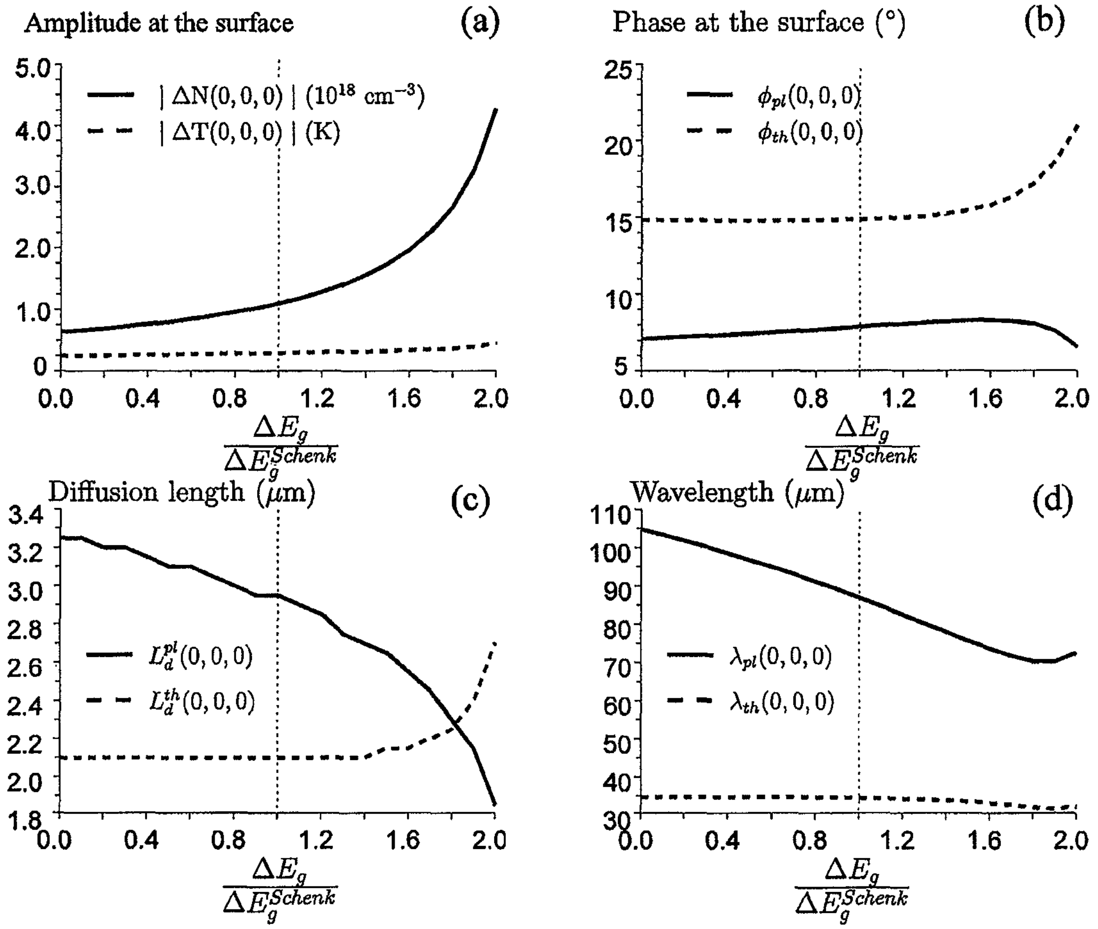

FIG. 10 illustrates variation in the amplitude (a), the phase (b), the diffusion length (c) and the wavelength (d) of the semi-analytical plasma wave (full lines) and thermal wave (dashed lines) as a function of BGN. The substrate doping is $10^{15}$ $cm^{-3}$ $\Delta E_g^{Schenk}$ is the BGN value obtained with Schenk's BGN model (also highlighted by the vertical dotted line).

Figure 11:
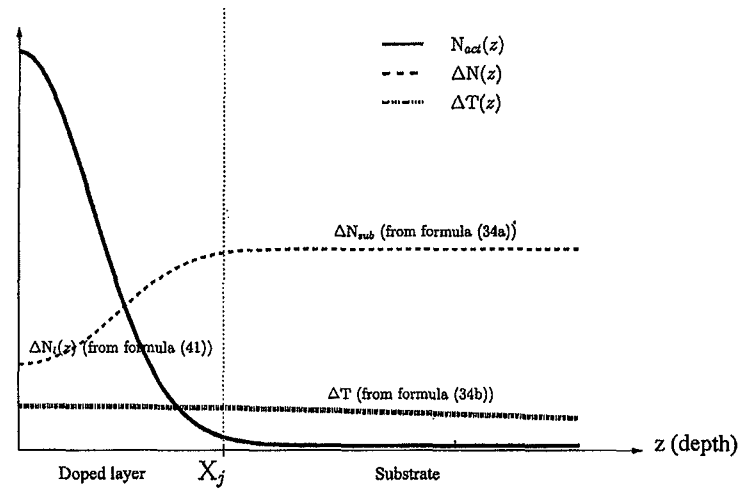

FIG. 11 provides a schematic illustration of a typical active doping profile and the pump-generated excess carrier and excess temperature profiles (The relative position of the excess carrier and excess temperature profiles is arbitrary).

Figure 12:
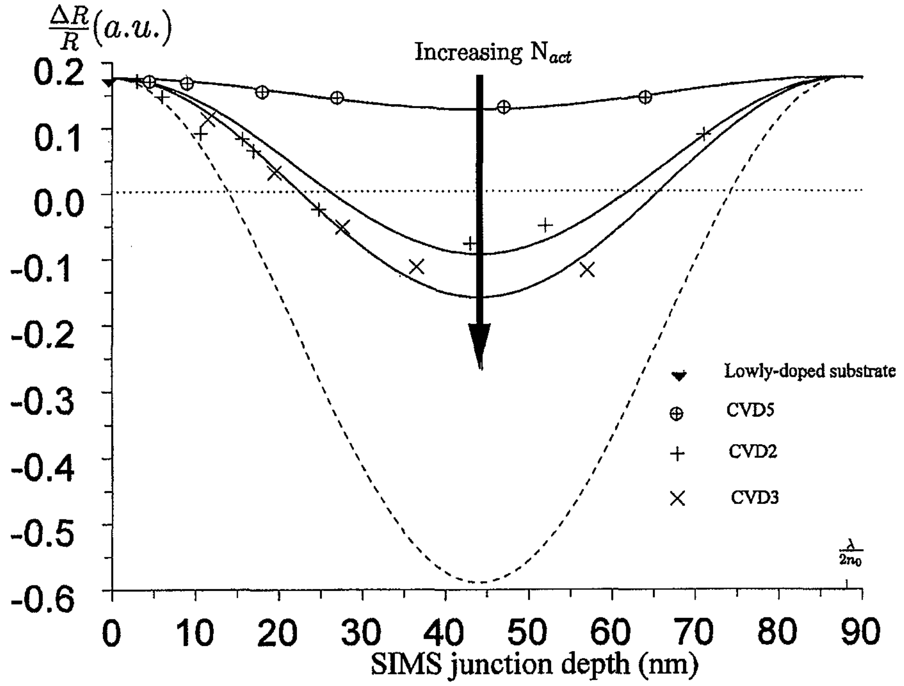
Figure 13:
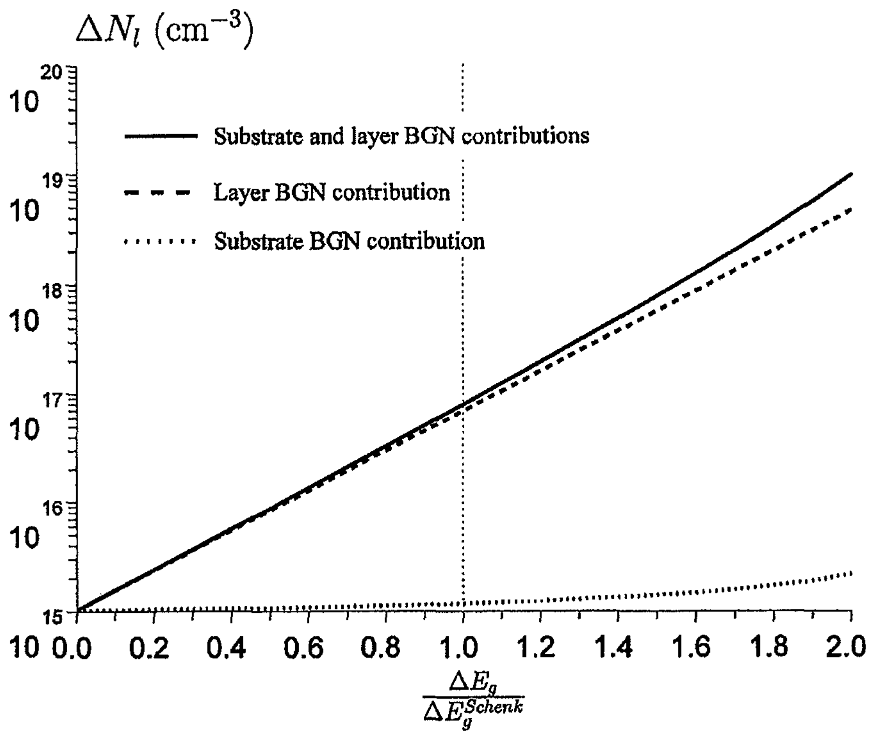

FIG. 12 illustrates a comparison of the experimental and theoretical behaviors of PMOR signals (TP) for box-like doping profiles with a varying junction depth. The sign of the signal is assigned following the measured phase, i.e. the sign is defined positive or negative according to whether the phase is 180° or 0° (CI convention). The fitting curves assume formula [45] for CVD2 and CVD3 and formulas [42] and [46] for CVD5, using the results obtained for lowly doped silicon in FIG. 9. The values of the sole fitting parameter $N_{act}$ are respectively $8\times10^{16}$ $cm^{-3}$ (CVD5), $9\times10'^{7}$ $cm^{-3}$ (CVD2) and $1\times10^{18}$ $cm^{-3}$ (CVD3). The dashed cosine indicates the theoretical behavior for $N_{act}=5\times10^{19}$ $cm^{-3}$ FIG. 13 illustrates the impact of BGN on $\Delta N_1$ for $N_{act}=10^{20}$ $cm^{-3}$ as obtained by formula (47) considering both layer and substrate BGN contributions (full line), the layer BGN contribution only (dashed line) and the substrate BGN contribution only (dotted line). $\Delta E_g^{Schenk}$ is the BGN value obtained with Schenk's BGN model (also highlighted by the vertical dotted line).

Figure 14A:
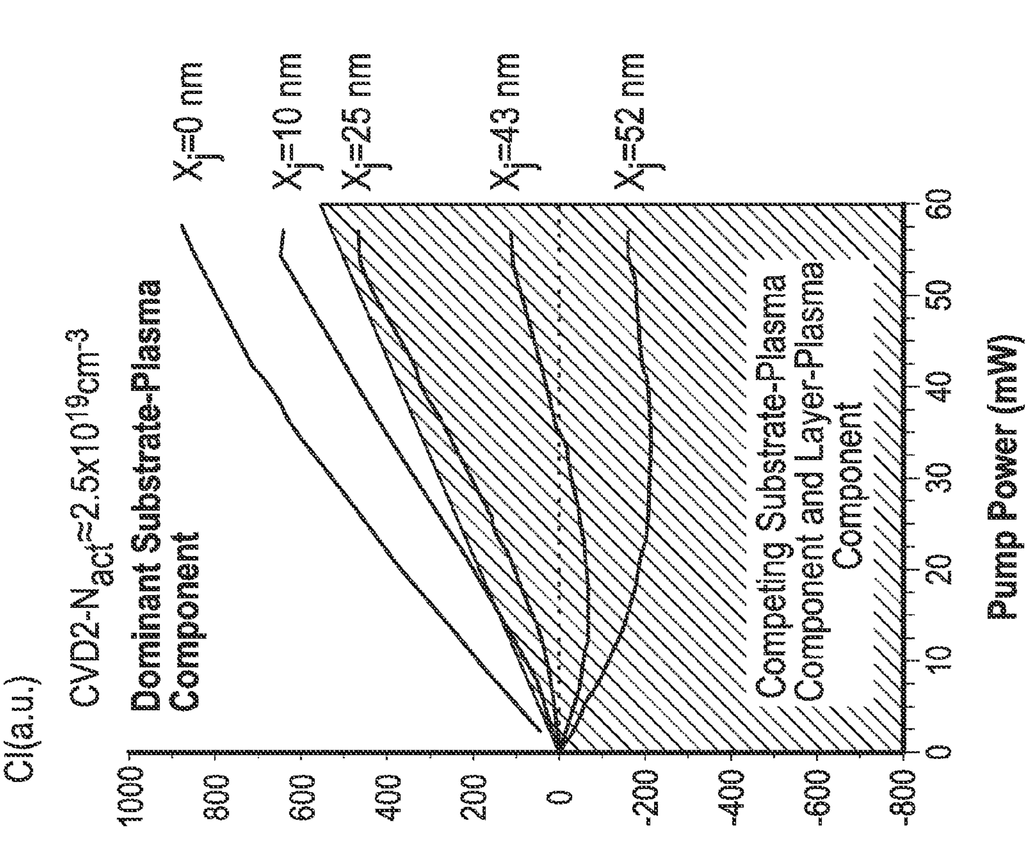
Figure 14B:
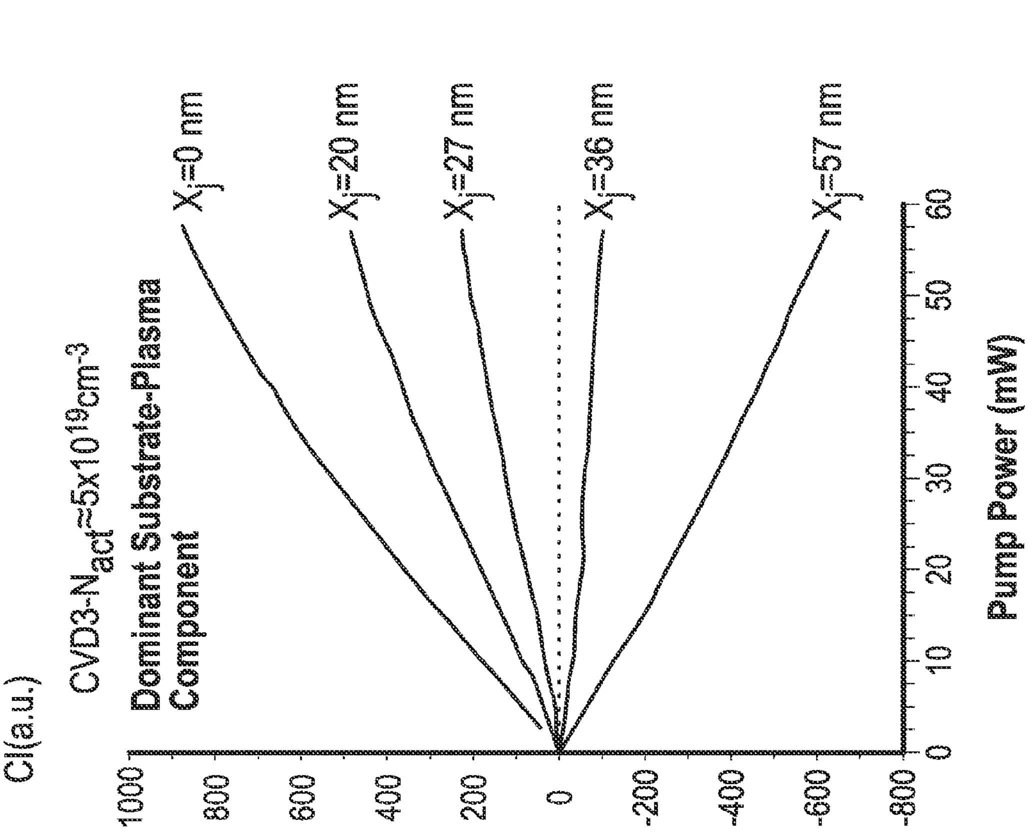

FIG. 14 illustrates the behavior of experimental power curves, i.e. variation in PMOR (CI) signals when the pump power is changed, on CVD2 (*a*) and CVD3 (*b*). For shallow layers and highly doped layers, the substrate plasma component is dominant (white background). Deeper, medium doped layers show competing substrate- and layer-plasma components (shaded background).

Figure 15A:
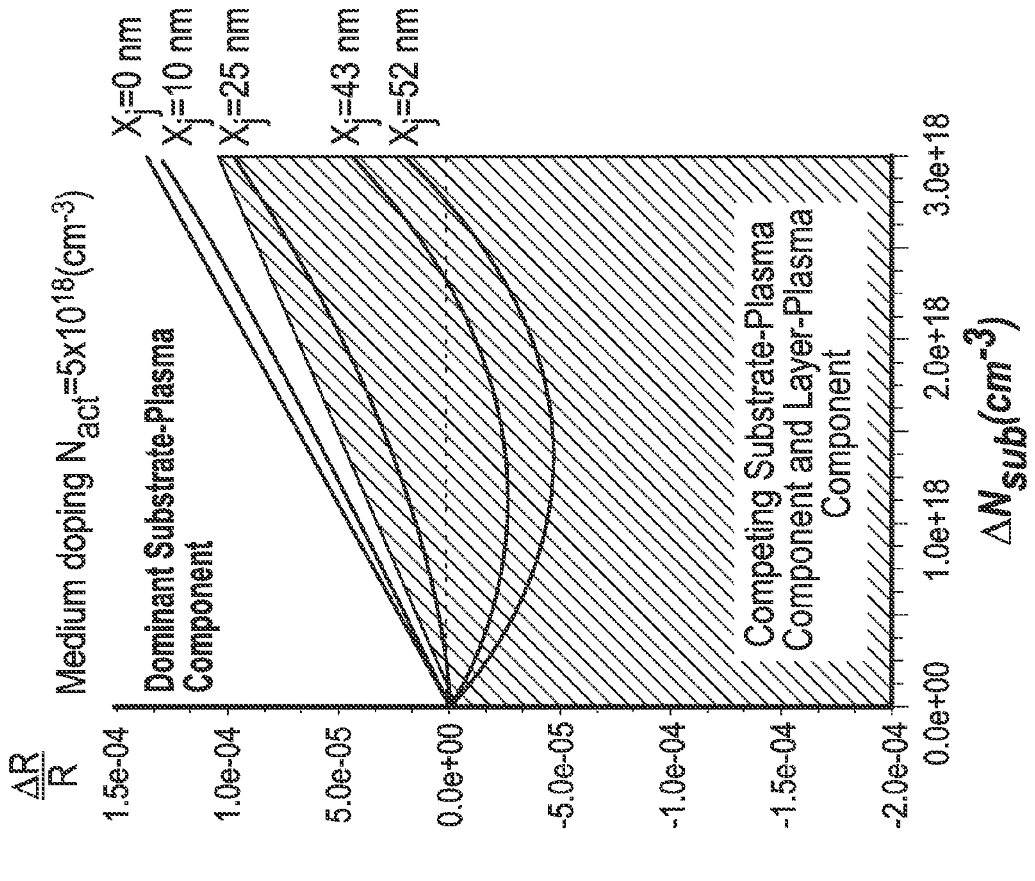
Figure 15B:
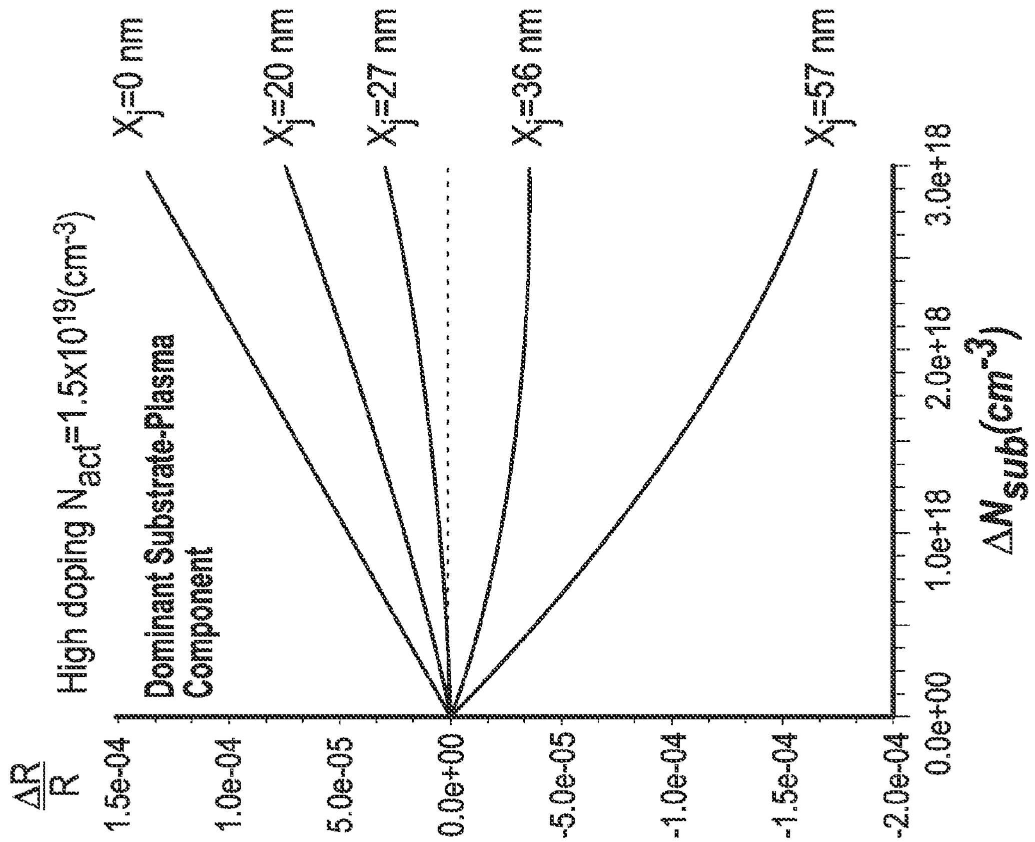

FIG. 15 illustrates the theoretical behavior of the power curves for medium doping (a) and high doping (b), following formula [45]. The thermal component amplitude is assumed to be a third of the substrate plasma component amplitude, i.e. $\delta\Delta T=(\beta/3)(1/m_e+1/m_h)\Delta N_{sub}$. The qualitative behavior of experimental power curves (FIG. 14) is easily recognized.

Figure 16:
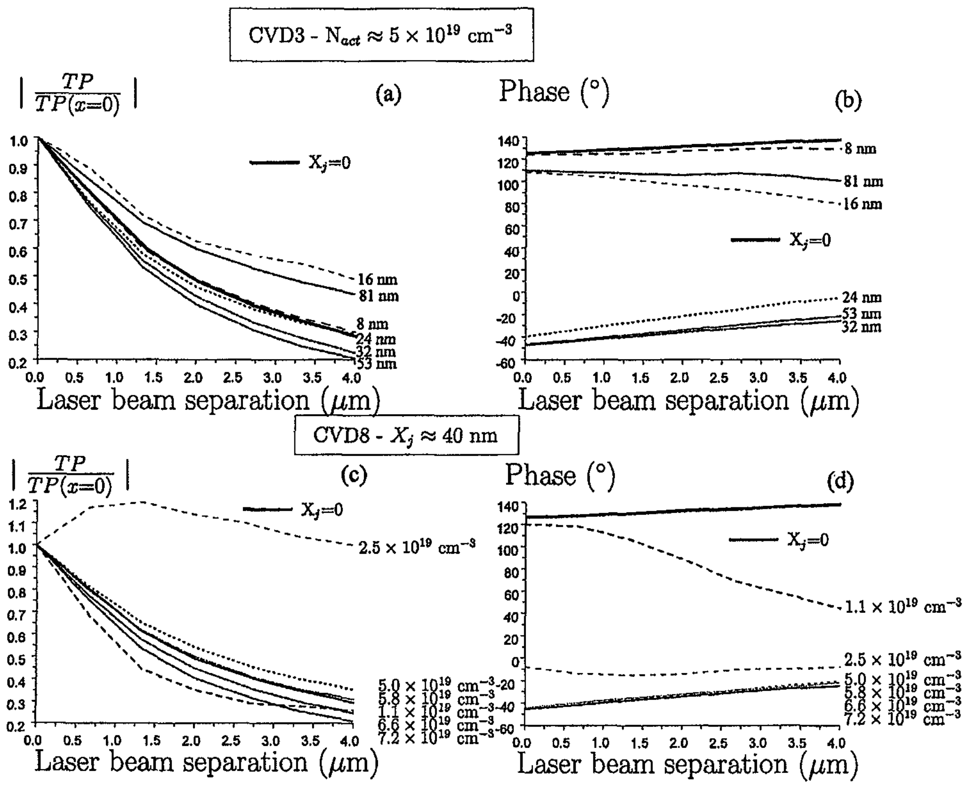

FIG. 16 illustrates experimental offset curves of the normalized amplitude (left) and the phase (right) of the TP signals measured on (top) the CVD3 matrix ($N_{act}$~$5\times10^{19}$ $cm^{-3}$ and different $X_j$ mentioned on the right) and (bottom) the CVD8 matrix ($X_j$~40 nm and different $N_{act}$ mentioned on the right).

Figure 17:
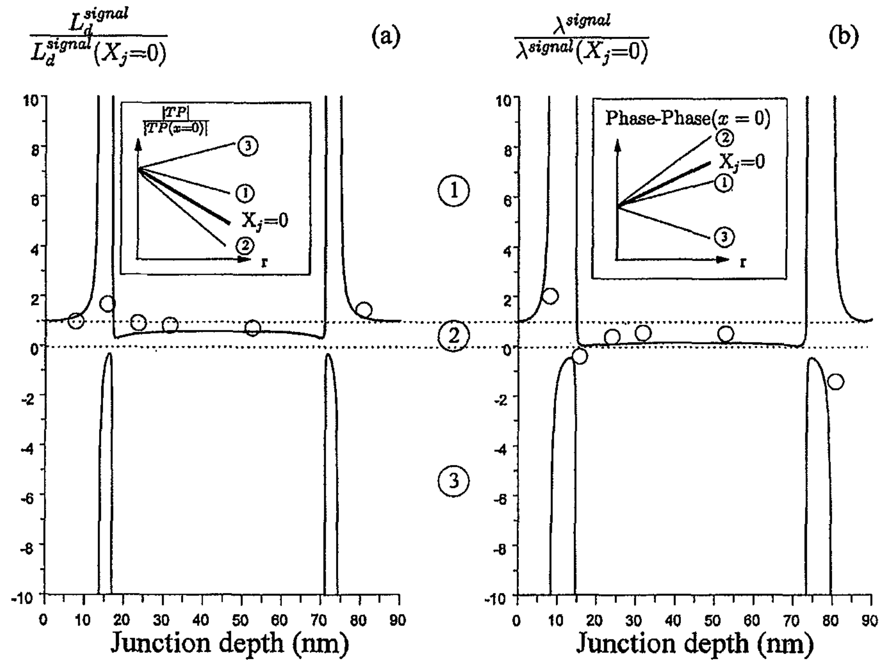

FIG. 17 illustrates the Behavior of (a) the lateral decay length and (b) the wavelength of the TP signals as a function of junction depth. The lines show the theoretically predicted behavior [formulas (50), (51) and (52)] for $\Delta N_1=0$ and the circles are the experimental values obtained on the CVD3 matrix. Both lengths can either be longer than on a lowly doped substrate (region 1), shorter (region 2) or even negative (region 3). The inset shows the typical behavior of the offset curve in each region.

Figures 18A, 18B:
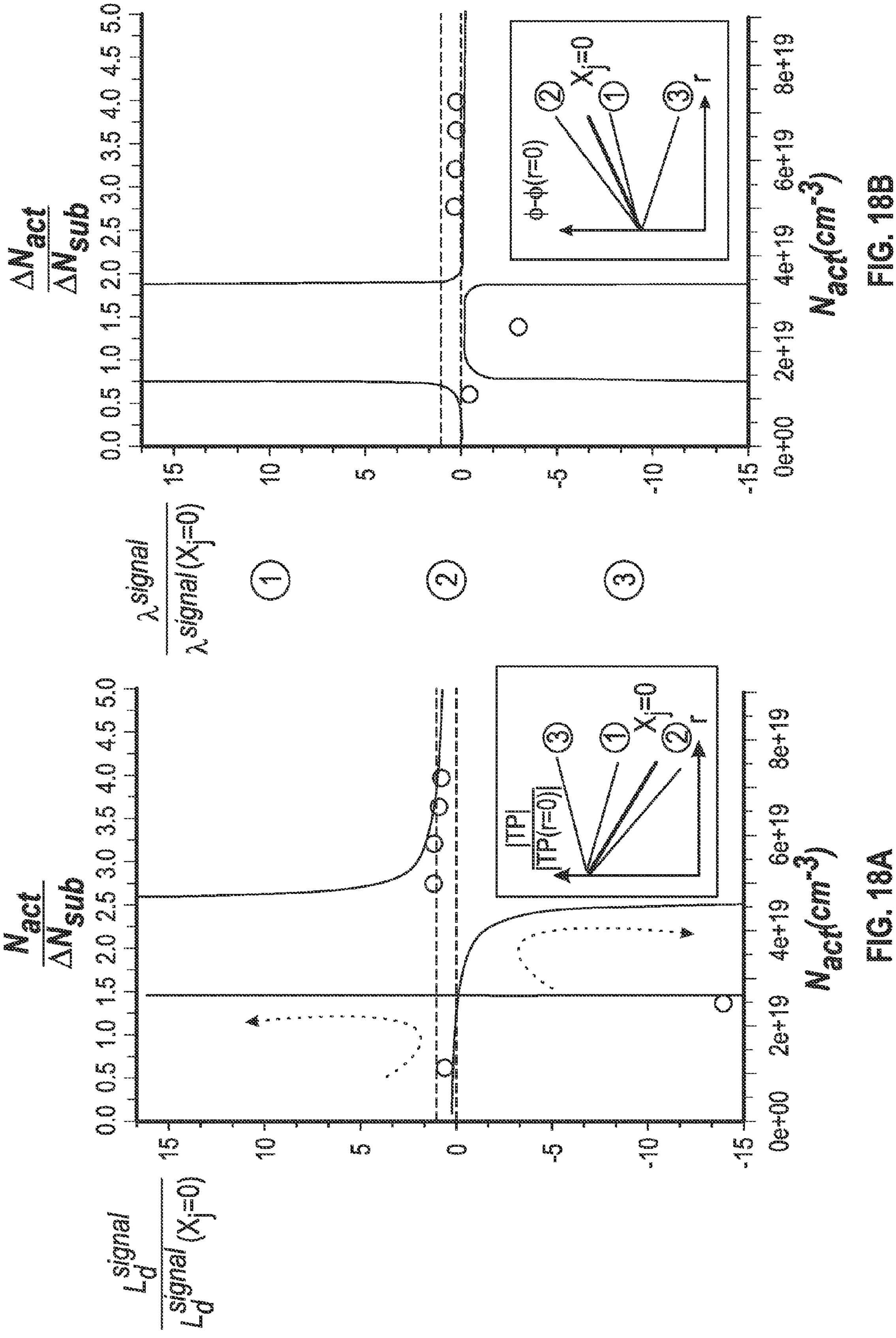

FIG. 18 illustrates the behavior of (a) the lateral decay length and (b) the wavelength of the TP signals as a function of $N_{act}$ for $X_j=40$ nm. The lines show the theoretically predicted behavior [formulas (50), (51) and (52)] for Xj=40 nm (top x-axis) and the circles are the experimental values obtained on the CVD8 matrix (bottom x-axis). Both lengths can either be longer than on a lowly doped substrate (region 1), shorter (region 2) or even negative (region 3). The inset shows the typical behavior of the offset curve in each region. The dotted arrows in (a) show the directions of the asymptotes.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF CERTAIN ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Figure 1:
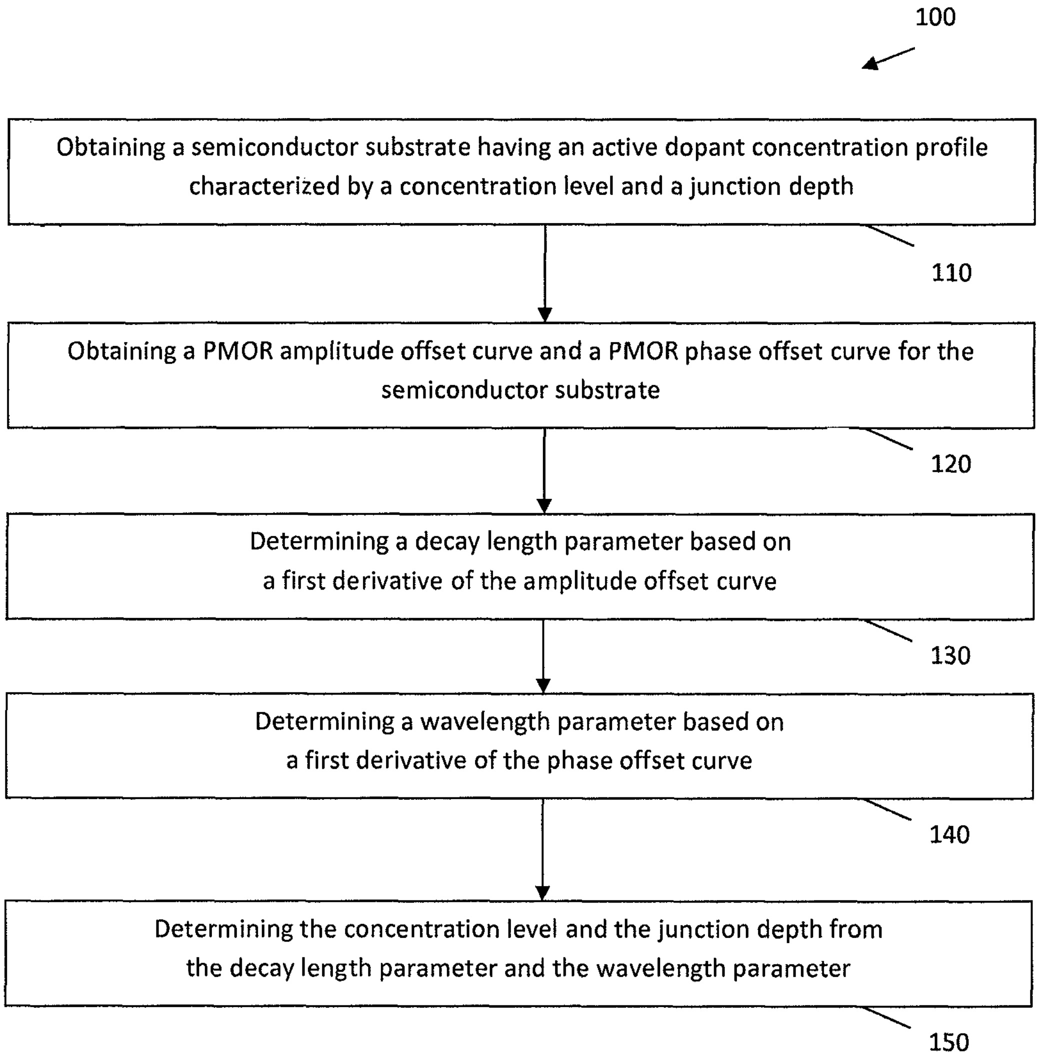
FIG. 1 illustrates a schematic overview of a method for determining a peak active dopant concentration and a junction depth, according to one embodiment.

In one embodiment, there is a method for determining an active dopant concentration profile of a semiconductor substrate based on optical measurements. Such optical measurements typically may be photomodulated reflectance measurements (PMOR). The photomodulated reflectance measurements according to one embodiment typically are optical amplitude or phase offset curves, as can be obtained for example using a thermo-probe measurement setup. The active dopant concentration profile for the semiconductor substrate typically comprising a peak concentration level, also referred to as concentration level, and a junction depth. Typical values for the peak concentration level that can be measured/determined using one embodiment may be $2.10^{18}/cm^3$ or higher. Typical junction depths that can be determined may be in the range 15 nm to 40 nm. By way of illustration, embodiments of the present invention not being limited thereto, an exemplary method will further be described with reference to FIG. 1, indicating optional and standard steps of the method. The exemplary method 100 comprises in a first step obtaining 120 a photomodulated reflectance (PMOR) amplitude offset curve and a photomodulated reflectance (PMOR) phase offset curve for the semiconductor substrate based on photomodulated reflectance (PMOR) measurements. Such obtaining 120 amplitude and phase offset curves may comprising obtaining data from previously measured data, e.g. obtaining the curves as input data. Alternatively or in addition thereto, obtaining 120 amplitude and phase offset curves may comprise obtaining 110 a semiconductor substrate having an active dopant concentration profile characterized by a concentration level and a junction depth, and experimentally determining through optically measuring a PMOR amplitude offset curve and a PMOR phase offset curve for the obtained semiconductor substrate.

The method 100 also comprises determining a decay length parameter 130 based on a first derivative, e.g. the slope, of the amplitude offset curve and determining a wavelength parameter 140 based on a first derivative, e.g. the slope, of the phase offset curve. The decay length parameter thereby may be given as the signal decay length $L^d_{signal}$ defined as $$L_d^{signal} = -\frac{|TP|}{\frac{\partial |TP|}{\partial x}}.$$

$L^d_{signal}$ is also referred to as the signal decay length, i.e. separation between pump laser and probe laser, needed for the amplitude to drop by a factor exp(1).

The wavelength parameter may be determined by the lateral distance $\lambda_{signal}$ defined as $$\lambda_{signal} = -2i\pi\frac{TP/|TP|}{\frac{\partial TP/|TP|}{\partial x}}.$$

$\lambda_{signal}$ is also referred to as the lateral distance, i.e. separation between pump laser and probe laser, needed for the phase to turn 360 degrees.

The exemplary method 100 also comprises determining 150 from the decay length parameter and from the wavelength parameter, e.g. from the signal decay length and the lateral distance, the (peak) concentration level and the junction depth of the active dopant concentration profile in the semiconductor substrate under study.

Determining the peak concentration level and the junction depth can be performed in a plurality of ways. In one particular embodiment, the peak concentration level and the junction depth can be determined based on the wavelength parameter and the decay length parameter in combination with a selected active dopant concentration profile.

One example of an active dopant concentration profile that could be used is a box-like active dopant concentration profile, resulting in an expression for the offset curve as described by the following equation:

$$TP(x) = G_{TP}\exp(-i\theta_{TP})\frac{4}{(n_0^2-1)}\Bigg[-\beta\left(\frac{1}{m_e}+\frac{1}{m_h}\right)\Bigg(\underbrace{\frac{|\Delta N_{sub}|^2}{N_{act}}(1-\cos(4\pi n_0 X_j/\lambda_{probe}))\exp\left(-\frac{2x}{L_d^{pl}}\right)}_{layer-plasma} + \underbrace{|\Delta N_{sub}|\cos(4\pi n_0 X_j/\lambda_{probe})\exp\left(-\frac{x}{L_d^{pl}}\right)}_{substrate-plasma}\Bigg)\exp(-i\varphi_{pl})\exp\left(-\frac{2i\pi x}{\lambda_{pl}}\right) + \underbrace{\delta|\Delta T_{surface}|\exp\left(\frac{-x}{L_d^{th}}\right)\exp(-i\varphi_{th})\exp\left(\frac{-2i\pi x}{\lambda_{th}}\right)}_{thermal}\Bigg]$$

More generally, an expression for the TP offset curves for a general active dopant concentration profile shape is given by $$R_{dc}^{Profile} = R_0\left\{1 - \frac{4\beta}{n_0^2 - 1}\frac{1}{m_h}\left[\begin{array}{c} P_{doping}(z=0) + \\ \int_{0+}^{+\infty}\frac{\partial P_{doping}(z)}{\partial z}\cos(4\pi n_0 z/\lambda_{^\wedge probe})\,dz \end{array}\right]\right\}$$

for p-type active doping profiles $$R_{dc}^{Profile} = R_0\left\{1 - \frac{4\beta}{n_0^2 - 1}\frac{1}{m_h}\left[\begin{array}{c} N_{doping}(z=0) + \\ \int_{0+}^{+\infty}\frac{\partial N_{doping}(z)}{\partial z}\cos(4\pi n_0 z/\lambda_{^\wedge probe})\,dz \end{array}\right]\right\}$$

for n-type active doping profiles, $$\Delta R_{ac}^{Profile}(r) = \frac{4R_0}{n_0^2 - 1}\Gamma_0\exp(-i\theta_0)\times \left\{\begin{array}{l} -\beta\left(\frac{1}{m_e} + \frac{1}{m_h}\right)\left[\begin{array}{l} \Delta N_{l1}(r, z=0) + \\ \int_{0+}^{+\infty}\frac{\partial \Delta N_{l1}(r, z)}{\partial z}\cos(4\pi n_0 z/\lambda_{^\wedge probe})\,dz \end{array}\right] \\ +\delta\Delta T_1(r) \end{array}\right\}$$

and $$\Delta N_l(z) = 0.5\left[\begin{array}{l} -P_{doping}(z) + \\ \sqrt{P_{dosing}^2(z) + 4\frac{\gamma_p^l(z)\gamma_n^l(z)}{\gamma_p^{sub}\gamma_n^{sub}}\exp\left(-\frac{E_g^l(z) - E_g^{sub}}{k_b T}\right)\Delta N_{sub}^2} \end{array}\right]$$

Combining the equation for the TP offset curves and the equations for the wavelength and decay length parameter, results in two equations with two unknowns, i.e. the peak concentration level and the junction depth. Based thereon, the peak concentration level and the junction depth can be derived therefrom.

In a second particular example, comparison is made from between a measured wavelength parameter and decay length parameter, and wavelength parameter and decay length parameters for known active dopant concentration profiles. Such known wavelength parameter and decay length parameters for known active dopant concentration profiles, and thus for known peak active dopant concentration and junction depth, may be provided as dataset, e.g. in a look up table or in a graphical representation. In case a graphical representation is provided, the wavelength parameter and the decay length parameter can be plotted on the graphical representation and by comparison with the corresponding parameters for the known active dopant concentration profile, the peak active dopant concentration and the junction depth can be derived.

Further features and advantages may be as illustrated in certain illustrative embodiments.

Figure 2:
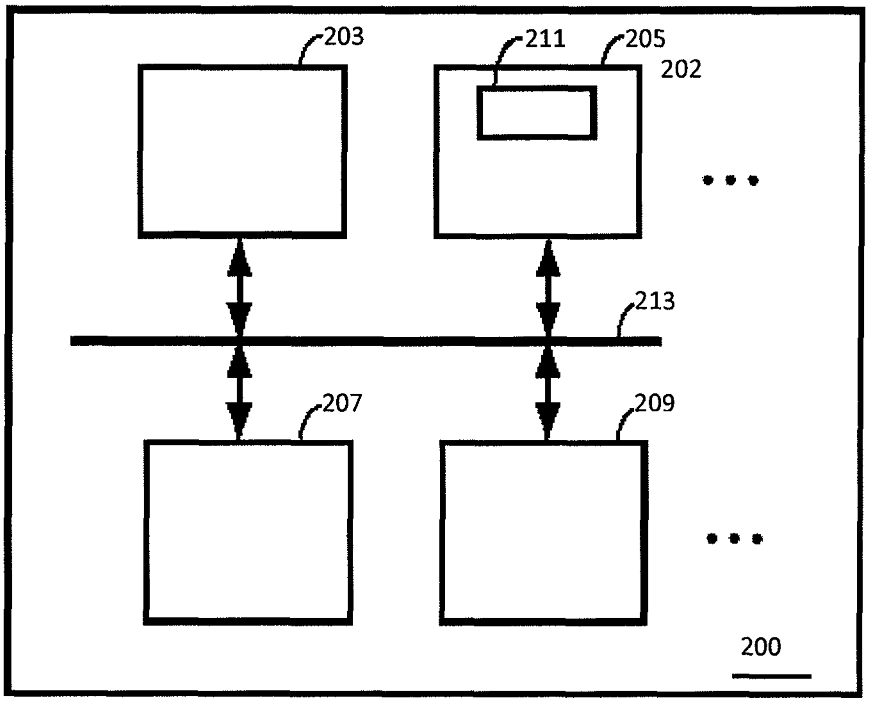
FIG. 2 illustrates a computing device as can be used for implementing a method for determining a peak active dopant concentration and/or a junction depth, according to one embodiment.

In one embodiment, there is a computing device for determining an active dopant concentration profile of a semiconductor substrate based on optical measurements. The computing device comprises an input means configured for obtaining a photomodulated reflectance (PMOR) amplitude offset curve and a photomodulated reflectance (PMOR) phase offset curve for the semiconductor substrate based on photomodulated reflectance (PMOR) measurements. It also comprises a processor configured for determining a decay length parameter based on a first derivative of the amplitude offset curve, for determining a wavelength parameter based on a first derivative of the phase offset curve, and for determining from the decay length parameter and from the wavelength parameter, the concentration level and the junction depth of the active dopant concentration profile. The processor may be any suitable processor, such as for example a dedicated processor or a processor that is programmed for performing the above tasks. It may be a single or multiple core processor. It may be one or more processors. By way of illustration, a computing device that may be used according to one embodiment may be as illustrated in FIG. 2. FIG. 2 illustrates a processing system 200 that includes at least one programmable processor 203 coupled to a memory subsystem 205 that includes at least one form of memory, e.g., RAM, ROM, and so forth. It is to be noted that the processor 203 or processors may be a general purpose, or a special purpose processor, and may be for inclusion in a device, e.g., a chip that has other components that perform other functions. The processing system may include a storage subsystem 207 that has at least one disk drive and/or CD-ROM drive and/or DVD drive. In some implementations, a display system, a keyboard, and a pointing device may be included as part of a user interface subsystem 209 to provide for a user to manually input information. Ports for inputting and outputting data also may be included. More elements such as network connections, interfaces to various devices, and so forth, may be included. The various elements of the processing system may be coupled in various ways, including via a bus subsystem 213, in the present example for simplicity a single bus, but will be understood to those skilled in the art to include a system of at least one bus. The memory of the memory subsystem may at some time hold part or all of a set of instructions that when executed on the processing system implement the steps of the method embodiments described herein.

Figure 3:
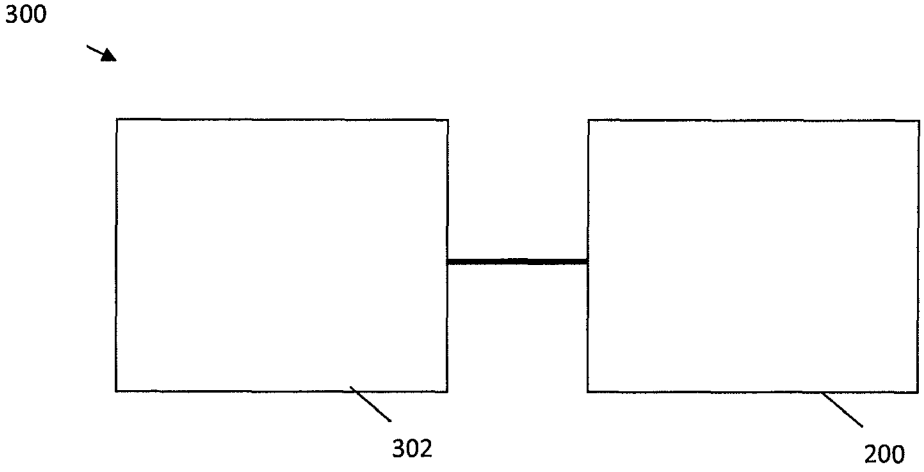
FIG. 3 illustrates a schematic representation of a system for determining a peak active dopant concentration and a junction depth, according to one embodiment.

One embodiment relates to a system for performing photomodulated reflectance. Such a system comprises a pump laser and a probe laser for obtaining photomodulated reflectance (PMOR) offset curve measurement data and a processing system for receiving photomodulated reflectance (PMOR) offset curve measurement data and for determining a decay length parameter based on a first derivative of the amplitude offset curve, for determining a wavelength parameter based on a first derivative of the phase offset curve, and for determining from the decay length parameter and from the wavelength parameter, the concentration level and the junction depth of the active dopant concentration profile. The processor may be a computing system as described above. The processor furthermore may be adapted for controlling the measurements to be performed with the optical components. FIG. 3 illustrates the overall system 300, wherein the PMOR measurement system 302 is connected to the computing device 200, for providing data input to the computing device and optionally for obtaining control commands from the computing device. An example of a PMOR measurement system may be a Therma-Probe® (TP) system for which the corresponding technique is described in "Non-destructive analysis of ultra shallow junctions using thermal wave technology" by Lena Nicolaides et al. in Review of Scientific Instruments, volume 74, number 1, January 2003. The TP technique is a high-modulation-frequency implementation of the PMOR technique. The system may for example be a ThermaProbe TP630XP tool (TP), a special implementation of PMOR with a pump laser power modulated at high frequency (1 MHz), fixed pump and probe laser wavelengths (resp. 790 nm and 670 nm), fixed pump and probe laser powers (resp. 13.5 mW and 2.5 mW) both focused onto an 0.5 µm beam radius, embodiments of the present invention not being limited thereto.

One embodiment relates to a computer program product for, when executing on a processing means, for example in a device according to the third aspect of the invention, carrying out one of the methods according to the first aspect of the invention. The corresponding processing system may be a computing device as described in the second aspect. In other words, methods according to one embodiment may be implemented as computer-implemented methods, e.g. implemented in a software based manner. Thus, one or more aspects of one embodiment can be implemented in digital electronic circuitry, or in computer hardware, firmware, software, or in combinations of them.

One embodiment relates to a data carrier for storing a computer program product for implementing a method as described above or to the transmission thereof over a wide or local area network. Such a data carrier can thus tangibly embody a computer program product implementing a method as described above. The carrier medium therefore may carry machine-readable code for execution by a programmable processor. In one embodiment, there is a carrier medium carrying a computer program product that, when executed on computing means, provides instructions for executing any of the methods as described above. The term "carrier medium" refers to any medium that participates in providing instructions to a processor for execution. Such a medium may take many forms, including but not limited to, non-volatile media, and transmission media. Non volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fiber optics, including the wires that comprise a bus within a computer.

By way of illustration and without being bound by theory, features and advantages of one embodiment may be understood from the following theoretical considerations, embodiments of the present invention not being limited thereby.

First, theoretical considerations for photomodulated reflectance are discussed. As mentioned in the introduction, PMOR is a pump-probe technique. During a PMOR measurement, a modulated pump laser modifies the local refractive index $\tilde{n}$ by a value $\Delta \tilde{n}$. A probe laser then measures this modification by means of a reflection. Here the different physical phenomena through which a pump laser can affect the refractive index are considered. The magnitudes of the different effects are compared to derive a quantitative expression for the (pump-induced) modulated refractive index.

Following Maxwell's wave equation, the complex refractive index of a lossy material at the wavelength $\lambda_{probe}$ of the probe laser reads $$\tilde{n} = n + ik = \sqrt{\tilde{\varepsilon}} = \sqrt{\tilde{\varepsilon}_{lattice}(\omega_{probe}) + \frac{i\sigma(\omega_{probe})}{\frac{\omega_{probe}\varepsilon_0}{\varepsilon_\sigma}}} \quad [1]$$

where n and k are respectively the real and imaginary parts of the complex refractive index, also called respectively the (real) refractive index and the extinction coefficient. $\tilde{\varepsilon}$ is the total dielectric constant, $\tilde{\varepsilon}_{lattice}$ is the dielectric constant of the intrinsic semiconductor (no free carriers available for conduction), σ is the frequency-dependent electrical conductivity, $\omega_{probe}$ is the probe optical angular frequency and $\varepsilon_0$ is the dielectric constant of vacuum. Equation [1] clearly highlights that there exist two contributions to the refractive index, (i) $\tilde{\varepsilon}_{lattice}$ and (ii) $\tilde{\varepsilon}_\sigma$. The first contribution, $\tilde{\varepsilon}_{lattice}$ accounts for all band-to-band (or inter-band) effects. $\tilde{\varepsilon}_{lattice}$ varies explicitly with temperature, electric field, and implicitly with free carrier concentration (via carrier-induced bandgap narrowing (BGN) and band-filling (BF)). The second contribution, $\tilde{\varepsilon}_\sigma$, contains the electrical conductivity (or the free-carrier) information, and is linked to all intra-band effects. It only varies with free carrier concentration.

The previous considerations show that the pump-induced variations in refractive index can be of three kinds. First, if the photon energy is higher than the sample bandgap, the pump laser generates a modulated excess carrier distribution $\Delta N(x,y,z,t)$, which impacts the refractive index (via both $\tilde{\varepsilon}_{lattice}$ and $\tilde{\varepsilon}_\sigma$). Second, a modulated excess temperature distribution or thermal wave $\Delta T(x,y,z,t)$ is also induced by the pump, which perturbs the refractive index (via $\tilde{\varepsilon}_{lattice}$). Finally, if the sample presents an electric field at equilibrium, the modulated excess carriers create a modulation of the electric field $\Delta \vec{E}(x,y,z,t)$. This modulated electric field will, in turn, impact the refractive index (via $\tilde{\varepsilon}_{lattice}$).

In all generality, the modulated change in refractive index therefore reads $$\Delta \tilde{n} = \underbrace{\underbrace{\frac{\partial n}{\partial \Delta N}\Delta N}_{Drude+BGN+BF} + \underbrace{\frac{\partial n}{\partial \vec{E}} \cdot \Delta \vec{E}}_{Pockels+Kerr}}_{electrorefraction} + i\underbrace{\left(\underbrace{\frac{\partial k}{\partial \Delta N}\Delta N}_{Drude+BGN+BF} + \underbrace{\frac{\partial k}{\partial \vec{E}} \cdot \Delta \vec{E}}_{Franz-Keldysh}\right)}_{electroabsorption} + \underbrace{\underbrace{\frac{\partial n}{\partial T}\Delta T}_{thermorefraction} + i\underbrace{\frac{\partial k}{\partial T}\Delta T}_{thermoabsorption}}_{thermooptical}. \quad [2]$$

$$\underbrace{\phantom{XXXXXXXXXXXXXXXXXXXXXXXXXXXXXXXXXXXXXXXXXXXXXXXXXXXXXXXX}}_{electrooptical}$$

In most studied cases, these effects have a very small magnitude (typical variation in refractive index $|\Delta \tilde{n}| < 10^{-3}$ at laser irradiance $\sim 10^6$ W·cm$^{-2}$). According to the experimental conditions (sample material, sample type, laser wavelengths, . . . ), some of the involved contributions can be even smaller and are therefore neglected here. The different effects are discussed below and discuss their relative magnitudes for Si in the red and NIR range are considered.

First electrooptical effects are considered.

The electrooptical effects account for the changes in complex refractive index due to either the presence of free carriers or of an electric field. Three free-carrier electrooptical phenomena are to be reported, namely (i) the Drude effect, (ii) the carrier-induced bandgap narrowing (BGN) effect and (iii) the band-filling (BF) effect. In addition, three electric-field effects are to be taken into account, namely the (i) Kerr, (ii) Pockels and (iii) Franz-Keldysh effects. These effects are discussed separately.

The Drude effect accounts for both electro-refraction (i.e. change in n) and electro-absorption (i.e. change in k) due to a variation in electrical conductivity, i.e. a variation in $\tilde{\varepsilon}_\sigma$. It is shown below that, at high optical frequencies like in red and NIR, the electrorefractive Drude effect is linear ($\Delta n \propto \Delta N$) and the electroabsorptive Drude effect is negligible.

The frequency-dependent Drude electrical conductivity due to charge carriers of charge q and mobility μ and in concentration $N_q$ is $$\sigma = \frac{q\mu N_q}{1 - i\omega_{probe}/\omega_{scatt}}. \qquad [3]$$

where $\omega_{scatt}=q/(m\mu)$ is the scattering frequency of the carriers and m their mass. In silicon, this scattering frequency is much smaller (~10 THz) than the optical frequencies $\omega_{probe}$ corresponding to red and NIR wavelengths (~1 PHz). In other words, the high-frequency electrical conductivity is purely imaginary (no resistive losses). Using formula [2] and assuming a real $\in_{lattice}$ the complex refractive index then reads, using first-order Taylor expansion, $$\tilde{n} = \sqrt{\varepsilon_{lattice} + \frac{i}{\omega_{probe}\varepsilon_0}\frac{q\mu N_q}{1 - i\omega_{probe}\frac{\mu m}{q}}} \approx \sqrt{\varepsilon_{lattice} - \frac{q^2}{\omega_{probe}^2\varepsilon_0 m}N_q} \approx n_0\left(1 - \frac{q^2}{2\omega_{probe}^2\varepsilon_0 n_0^2 m}N_q\right) \qquad [4]$$

where $n_0$ is the semiconductor refractive index at equilibrium. If electrons and holes are generated in equal densities, the first derivatives of the real and imaginary refractive indices can therefore be written respectively $$\left.\frac{\partial n}{\partial \Delta N}\right|_{Drude} = \underbrace{-\frac{q^2}{2\omega_{probe}^2\varepsilon_0 n_0}}_{\beta}\left(\frac{1}{m_e} + \frac{1}{m_h}\right) \text{ and} \qquad [5]$$

$$\left.\frac{\partial k}{\partial \Delta N}\right|_{Drude} \approx 0 \qquad [6]$$

where β is the so-called Drude coefficient and $m_e$ and $m_h$ are respectively the electron and hole effective masses. For completeness, notice that equation [6] is strictly only valid in visible and NIR wavelengths. Deeper in the infra-red, the extinction coefficient of Si strongly increases with free carrier concentration. This is often referred to as free carrier absorption (FCA). Notice also that, besides being indeed very small in visible and NIR wavelengths, $\partial k/\partial \Delta N|_{Drude}$ is also always positive. In other words, the Drude contributions to the real and imaginary refractive indices have opposite signs and different orders of magnitude.

To sum up, the variation in refractive index is real and proportional to the generated free carrier concentration.

Figure 4A:
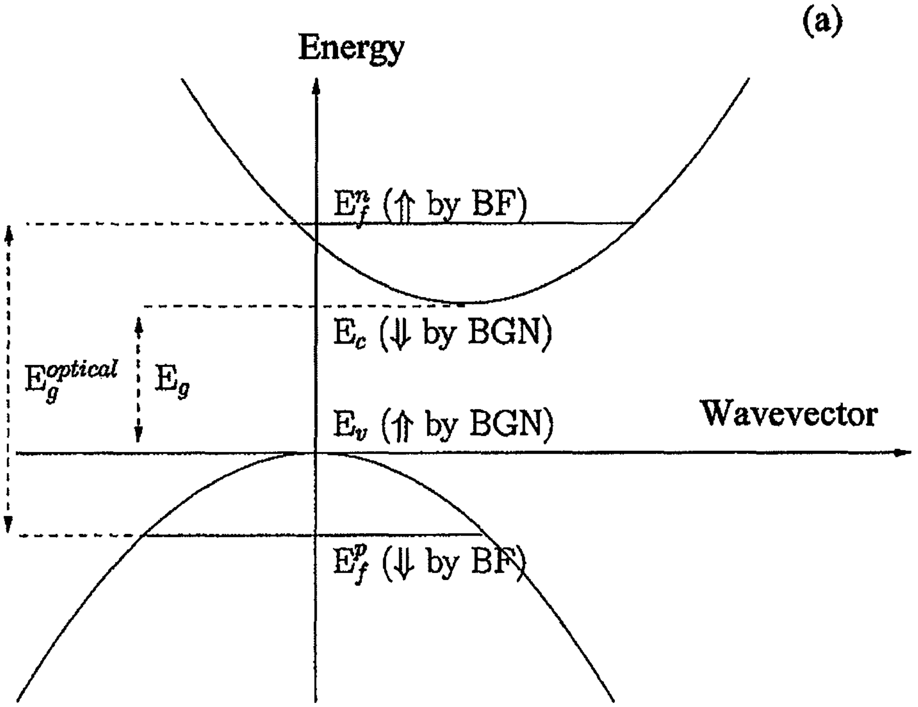

Now, the carrier-induced bandgap narrowing (BGN) effect is discussed. When injecting free carriers into a silicon sample, the band structure of the lattice is modified FIG. 4*a*. FIG. 4*a* illustrates a schematic overview of the band structure of Si. The impact of BGN and BF effects are indicated between brackets. $E_c$ is the lowest energy level of the conduction band and $E_v$ the highest energy level of the valence band, the bandgap is $E_g=E_c-E_v$. $E_f^n$ and $E_f^p$ are respectively the electron and hole quasi-Fermi levels, the optical bandgap is $E_g^{optical}=E_f^n-E_f^p$. It is implicitly assumed in this figure that the semiconductor is highly degenerated ($E_f^n$ and $E_f^p$ are located in the bands). The injected free carriers renormalize the sample bandgap $E_g$, which, in turn, modifies the complex refractive index via $\tilde{\in}_{lattice}$. This carrier-induced change in the refractive index has not been taken into account in previous optical models for PMOR. It is checked whether this effect is negligible.

Figure 4B:
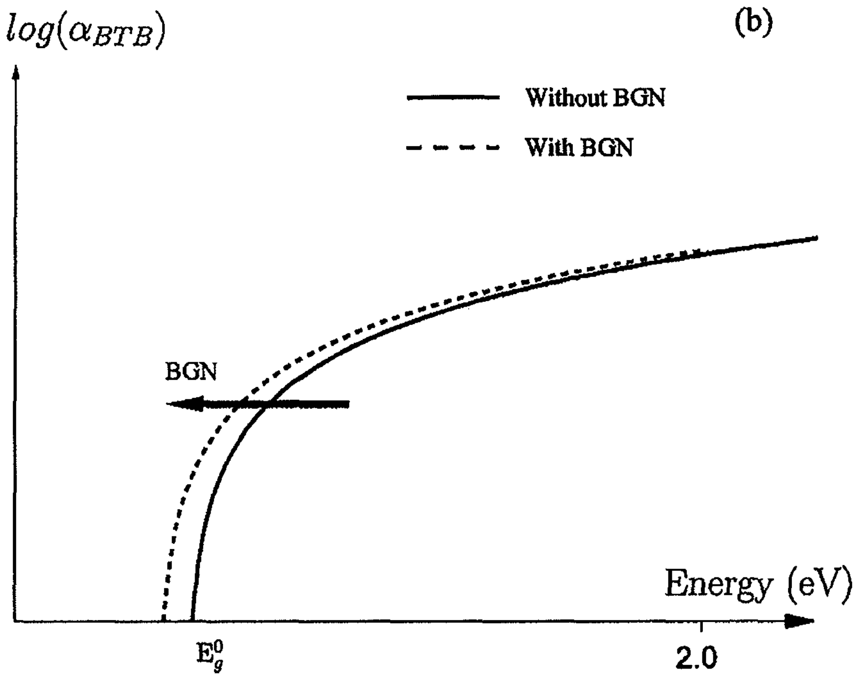

Physically, the change in band-to-band absorption coefficient $\alpha_{BTB}$ stems from the increase in available states for electron-hole pair generation for a fixed wavelength. Above the indirect absorption edge $E_g$, the band-to-band absorption coefficient is proportional to $(\hbar\omega_{probe}-E_g)^2$. A narrowed bandgap induces therefore an increased absorption coefficient [see FIG. 4*b*], i.e. an increased extinction coefficient. As for the variation in refractive index, it follows the Kramers-Kronig (KK) relationship. FIG. 4*b* illustrates the impact of BGN on the variation in $\alpha_{BTB}$ with photon energy. $E_g^0$ is the bandgap energy before BGN. BGN is assumed to cause a rigid shift in the indirect absorption edge, effective up to a 2 eV photon energy.

In order to model this effect, following equation is used $$\left.\frac{\partial \tilde{n}}{\partial \Delta N}\right|_{BGN} = \left(\frac{\partial n}{\partial E_g} + i\frac{\partial k}{\partial E_g}\right)\frac{\partial E_g}{\partial \Delta N}. \qquad [7]$$

Two terms therefore need to be quantified. The first term, $\partial E_g/\partial \Delta N$, is known and has been modeled. Shaheed's experimental BGN fitting is used since doping is here not relevant. This causes some inconsistence problem with the transport model where Schenk's BGN model is used, but it is believed to be more accurate since it is a direct fitting of the experimental BGN due to excess carriers. The second term, $(\partial n/\partial E_g+i\partial k/\partial E_g)$, has not been fully modeled yet. The following approximation reasoning is used to quantify it. Using the experimental k spectrum measured on undoped Si, it is assumed that the excess free carriers rigidly shift the indirect absorption edge only in the 0 to 2 eV range. An estimation of $\partial k/\partial E_g$ can then be obtained directly by comparison of the shifted and unshifted k spectra. Similarly, $\partial n/\partial E_g$ can be obtained by comparing the KK transforms of respectively the shifted and unshifted spectra. For the sake of completeness, notice that it is actually the imaginary dielectric constant which is KK transformed. The results obtained at 1.85 eV photon energy are shown in FIG. 5 for both positive and negative variations in bandgap. For bandgap narrowing (negative variation in bandgap), it is observed that $\partial n/\partial E_g \approx \partial k/\partial E_g \approx -0.05\ eV^{-1}$. This interestingly means that at $\partial k/\partial \Delta N|_{BGN} \approx \partial n/\partial \Delta N|_{BGN}$. This result is significantly different from the Drude contribution where the real and imaginary parts have different orders of magnitude and opposite signs. Notice that, due to the numerical KK transform, the obtained ∂n is quite noisy. However, in the first hundred meV, a linear relationship is clearly observed (carrier-induced BGN in silicon is always smaller than approximately 0.1 eV).

The resulting $\partial \tilde{n}/\partial \Delta N|_{BGN}$ and $\partial \tilde{n}/\partial \Delta N|_{Drude}$ are compared in FIG. 6 as a function of excess carrier concentration, assuming $1\times10^{18}\ cm^{-3}$ background carrier concentration (this represents the DC components of the probe- and pump-generated excess carriers). The real and imaginary contributions are analyzed separately. On the one hand, even though the real contributions of the Drude and BGN effects are of the same order of magnitude, the Drude effect dominates independently from the excess carrier concentration. On the other hand, only the BGN effect has a non negligible imaginary contribution. Adding the BGN to the Drude contribution gives rise to a change in complex refractive index with almost equal real and imaginary parts. Nevertheless, as from comparison with experimental results the present analysis seems to strongly overestimates the BGN effect, the impact of BGN on the refractive index is neglected, as is usually done in PMOR models.

The Burstein shift or band-filling (BF) effect is also considered.

Similar to the BGN effects, when excess carriers are injected into silicon, the optical bandgap also suffers from modifications due to BF, as indicated in FIG. 4*a*. Indeed, when injecting excess carriers, the states at the bottom of the conduction band are filled and therefore no longer available for absorption by a valence electron. Furthermore, states at the top of the valence band empty under injection, leading to further reduction in absorption coefficient. In other words, the injected carriers widen the optical bandgap, which in turn reduces the absorption coefficient. However, it is not expected to see any Burstein shift in the PMOR experiments. This effect is indeed only effective when a carrier density is reached such that the carrier distributions are degenerate. It is usually assumed that this occurs when the electron (resp. hole) quasi-Fermi level lies $4k_bT$ above (resp. below) the bottom of the conduction band (resp. the top of the valence band), $k_b$ being Boltzmann's constant and T the lattice temperature. In Si at 300K, this corresponds respectively to an electron concentration of $1.7\times10^{20}$ $cm^{-3}$ and a hole concentration of $6.4\times10^{19}$ $cm^{-3}$. These densities will never be reached in either TP or CI in the current experiments. In other words, unlike shown in FIG. 4*a*, the electron and hole quasi-Fermi levels never lie in the bands but are always located within the bandgap. This effect is therefore neglected here. It is, however, important to keep this effect in mind in the case of small effective mass semiconductors (such as InSb), where this effect can be considerable.

The Pockels, Kerr and Franz-Keldysh effects are also discussed.

The Pockels and Kerr effects are respectively first- and second-order electro-refractive effects due to the presence of an electric field. The Franz-Keldysh effect accounts for electro-absorption due to the presence of an electric field (enhanced band-to-band absorption under high electric field due to band bending). These effects impact $\in_{lattice}$. A very thorough investigation of these phenomena has been conducted by Aspnes. These effects can be taken advantage of in order to quantify the electric field at the junction between two semiconductors or at the surface of a semiconductor sample.

In the case of TP and CI, these three effects can be neglected for two reasons. First, they are significant only at wavelengths very close to the (direct or indirect) bandgap of the studied semiconductor. Second, for reflection to be sensitive to an electric field, the in-depth extension of the electric field needs to be of the order of the wavelength. The current model deals with the built-in electric field at the junction between two doped Si regions. Under intense illumination, the extension of such an electric field is only limited to a few nanometers close to the junction. The Debye length, giving the screening length of an electric field by free carriers in density $N_q$ is indeed $L_{Debye}=\sqrt{(\in_{lattice}k_bT)/(q^2N_q)}$, i.e. only a couple of nanometers for an excess carrier concentration around $10^{18}$ $cm^{-3}$. In other words, the modulated electric field $\Delta\vec{E}$ (x,y,z,t) generates a very local peak of modulated refractive index, which induces negligible reflection. The Pockels, Kerr and Franz-Keldysh effects are therefore not considered in this model.

Further also thermooptical effects are considered.

The complex refractive index also varies due to the generated excess temperature (via $\tilde{\in}_{lattice}$). These variations stem mostly from the thermally induced BGN and partly from thermal expansion. These effects are rather complex to model physically. It is therefore decided to use a fitting of experimental data. This fitting also shows that the thermoabsorption is negligible with respect to thermorefraction. In the present model, therefore simply use is made of a linear thermorefractive effect such that $$\frac{\partial\tilde{n}}{\partial T}=\delta. \qquad [8]$$

In summary, for TP and CI, the electrooptical and thermooptical effects in silicon can be summarized by summing up formulas [5] and [8]

$$\Delta\tilde{n}=\Delta n=\frac{\partial n}{\partial\Delta N}\Delta N+\frac{\partial n}{\partial T}\Delta T=-\beta\left(\frac{1}{m_e}+\frac{1}{m_h}\right)\Delta N+\delta\Delta T. \qquad [9]$$

This modulated refractive index variation induces the modulated probe reflectance, i.e. the PMOR signal, further discussed below. Formula [9] is in agreement with the commonly used optical model for PMOR. It has, however, to be kept in mind that formula [9] assumes negligible impact of BGN on the complex refractive index. This gives acceptable agreement with the experimental PMOR data discussed in experiments illustrating one embodiment.

Now theoretical considerations for modeling PMOR in modulated reflectance are discussed.

Formula [9] gives the final modulated refractive index generated by the pump laser. Implicit in this formula is the dependence of all the modulated components on depth. Here the final modulated reflectance of the probe laser is derived given a certain modulated refractive index profile for a normally incident probe laser and a system lying in air. Three cases are considered. First, homogeneous samples are studied. In this case, the modulated refractive index only varies at the top surface. Second, the case of a box-like refractive index profile is considered, where the modulated refractive index shows two abrupt variations, one at the top surface and one at a depth $X_j$, which is called the junction depth. Finally, a formula is derived for a general profile shape of the modulated refractive index.

First the modulated reflectance due to a modulated refractive index which is flat everywhere in the sample is discussed. In the case of TP and CI in Si, this would be the case of a homogeneously doped silicon sample as long as the variations with depth in excess carriers and excess temperature are negligible. It can be verified that these variations are indeed small at the scale of the probe wavelength $\lambda_{probe}$ (see the typical diffusion length scales in Section IV). Using Fresnel's reflection formula and neglecting all second-order terms in $\Delta n$ or $\Delta k$, the reflectance reads $$R=\left|\frac{1-(n_0+ik_0)-(\Delta n+i\Delta k)}{1+(n_0+ik_0)+(\Delta n+i\Delta k)}\right|^2 \qquad [10]$$

$$\approx\underbrace{\left|\frac{1-(n_0+ik_0)}{1+(n_0+ik_0)}\right|^2}_{R_0}\left|\left(1-\frac{\Delta n+i\Delta k}{1-n_0-ik_0}\right)\left(1-\frac{\Delta n+i\Delta k}{1+n_0+ik_0}\right)\right|^2$$

-continued $$\approx R_0\left|1-\frac{2}{(1-n_0-ik_0)(1+n_0+ik_0)}(\Delta n+i\Delta k)\right|^2$$

$$\approx R_0\left[1-\frac{4}{(1-n_0^2+k_0^2)^2+4n_0^2k_0^2}((1-n_0^2+k_0^2)\Delta n-2n_0k_0\Delta k)\right]$$

where $R_0$, $n_0$ and $k_0$ are respectively the reflection coefficient, the (real) refractive index and the extinction coefficient, all at equilibrium. Given that, at red and NIR wavelengths in Si, $k_0 \ll n_0$, the final PMOR signal on a homogeneous semiconductor sample simply reads $$\left.\frac{\Delta R}{R_0}\right|_{homogeneous}=\frac{R-R_0}{R_0}=\frac{4}{(n_0^2-1)}\Delta n \qquad [11]$$

It is interesting to notice that Δk does not appear in formula [11]. This is not a consequence of formula [9] but of the fact that the impact of Δk is always proportional to $k_0$, which is very small in silicon in the red and NIR range. In other words, even if it does exist, Δk never has a significant impact on the modulated reflectance of a homogeneous silicon sample in the red and NIR range.

An alternative formulation of the same problem has been derived by Seraphin by directly differentiating Fresnel's reflection formula. Noticing that, in the case of a weakly absorbing medium such as Si in the red and NIR, Seraphin's α coefficient is dominant and equal to $2/(n_0(n_0^2-1))$, it is easy to check that both formulations are equivalent.

The problem of a modulated refractive index profile which has only two abrupt transitions is now considered (box-like profile), one at the top surface and one at the junction depth $X_j$. This is an attractive situation since such profile shape in experiments discussed below will be the modulated refractive index profile on a box-like doping profile.

The studied situation is depicted in FIG. 7. FIG. 7 illustrates a box-like modulated refractive index profile showing two abrupt variations, respectively at the surface and at the interface, whereby the interface is located at a depth Xj assumed to be much smaller than the penetration depth of the probe laser ($1/\alpha_{probe}$). The modulated refractive index has a value $\Delta n_l+i\Delta k_l$ in the box and a value $(\Delta n_{sub}+i\Delta k_{sub})$ below the layer. The refractive index of the sample at equilibrium is uniform and equal to $(n_0+ik_0)$. If one assumes that the magnitude of the modulated refractive index is too small to cause multireflections in the box, the modulated reflectance is simply the coherent sum of the two reflections occurring respectively at the surface and at the interface. Further assuming that $X_j$ is much smaller than the penetration depth of the probe laser $1/\in_{probe}$, the total reflectance is $$R=\left|\tilde{r}_l+\tilde{r}_{sub}\tilde{t}_l^{\uparrow}\tilde{t}_l^{\downarrow}\exp(4i\pi n_0X_j/\lambda_{probe})\right|^2= R_0\left\{1-\frac{4}{(1-n_0^2+k_0^2)^2+4n_0^2k_0^2}\right. [(1-n_0^2+k_0^2)\cdot(\Delta n_l-\cos(4\pi n_0X_j/\lambda_{probe})(\Delta n_l-\Delta n_{sub}))+ \sin(4\pi n_0X_j/\lambda_{probe})(\Delta k_l-\Delta k_{sub})- 2k_0n_0(\Delta k_l-\sin(4\pi n_0X_j/\lambda_{probe})(\Delta n_l-\Delta n_{sub})- \left.\cos(4\pi n_0X_j/\lambda_{probe})(\Delta k_l-\Delta k_{sub}))]\right\} \qquad [12]$$

where $\tilde{r}_l$, $\tilde{r}_{sub}$ are the reflection coefficients respectively at the surface and the interface, $\tilde{t}_l^{\downarrow}$ and $\tilde{t}_l^{\uparrow}$ are the transmission coefficients through the surface respectively for incoming and outgoing light. All second-order terms in refractive index variations were neglected. Assuming again that $k_0 \ll n_0$, the modulated reflectance is $$\frac{\Delta R}{R_0}=\frac{4}{(n_0^2-1)}\begin{pmatrix}\Delta n_l-\cos(4\pi n_0X_j/\lambda_{probe})(\Delta n_l-\Delta n_{sub})+\\ \sin(4\pi n_0X_j/\lambda_{probe})(\Delta k_l-\Delta k_{sub})\end{pmatrix} \qquad [13]$$

Formula [13] indicates that the variation in extinction coefficient which was calculated for the carrier-induced BGN effect, would strongly impact the Xj-dependence of the PMOR signals. To pure cosine dependence, this would superimpose a sine dependence of roughly the same amplitude. Yet, in the experiments it is shown that experimental data present a cosine behavior. The calculated variation in extinction coefficient must therefore be strongly overestimated, as already pointed out above.

In other words, neglecting the variation in extinction coefficient, the modulated reflectance becomes $$\left.\frac{\Delta R}{R}\right|_{box}=\frac{4}{(n_0^2-1)}(\Delta n_l-\cos(4\pi n_0X_j/\lambda_{probe})(\Delta n_l-\Delta n_{sub})) \qquad [14]$$

It is to be noticed that, if $X_j=0$, formula [14] nicely reduces to formula [13]. Second, due to the interference between the surface and interface reflections, the PMOR signal on a box profile can be negative even though the modulated refractive index is positive everywhere. This is very different from the case of a homogeneous sample, where the sign of the modulated reflectance always follows the sign of Δn.

Finally, it is also important to underline that it has been assumed that only the modulated refractive index shows a variation at the interface. The equilibrium refractive index is indeed considered uniform. It can be shown that the impact of the equilibrium free carriers (i.e. due to the active dopants) on the PMOR signal is negligible.

In the case of an arbitrary modulated refractive index (arbitrary profile), the modulated reflectance is the coherent sum of the reflections occurring at all depths z of the profile. Under the same assumptions as those needed to derive formula [14], it can be shown that the PMOR signal reads $$\left.\frac{\Delta R}{R}\right|_{profile}=\frac{4}{(n_0^2-1)}\left[\Delta n(z=0)+\int_{0+}^{\infty}\frac{\partial\Delta n(z)}{\partial z}\cos(4\pi n_0z/\lambda_{probe})dz\right]. \qquad [15]$$

It can be easily checked that in the case of a box-like profile, formula [15] reduces to [14].

It is to be mentioned that Aspnes has generalized Seraphin's modulated reflectance theory to a spatially (depth-) dependent modulated refractive index. The equivalence of the present formulation and Aspnes' can easily be proven by integrating [15] by part. Like in Aspnes' formulation, this leads the integrand to being proportional to the modulated refractive index Δn(z) rather than its first derivative. Notice that, practically speaking, formula [15] is more suited for numerical integration than that of Aspnes.

In the following, the electrothermal transport theory in homogeneous silicon substrates and thereafter in doped layers is discussed.

From the above it is clear that in order to understand the behavior of PMOR signals on silicon one needs to derive the excess carrier and temperature profiles generated by the pump laser. Here the transport theory of excess carriers and heat under the pump laser beam in the case of a homogeneously doped silicon sample. It will be shown that no transport takes place in a shallow doped layer. The carrier and heat transport occurs in the bulk of the material. After transport in the bulk, the electrostatics charges the layer with excess carriers. It also appears that the thermoelectric effects have hardly ever been discussed in the framework of PMOR. Wagner incorporated these effects a posteriori in his model to show that they should be negligible. Opsal also studied the effect of thermodiffusion of carriers (similar to a Seebeck effect). However, only constant thermodiffusion coefficient was considered. Here these thermoelectric effects are taken into account a priori and then show consistently when they are negligible. The bandgap narrowing quasi-drift is also included in a generalized ambipolar diffusion equation for the carrier transport. The one- and three-dimensional solutions of the obtained equations are discussed. The one-dimensional solution offers qualitative understanding of the carrier and temperature behaviors with analytical expressions. The three-dimensional solution gives quantitative but numerical information. Both the optical model and the transport model of PMOR involve a modulation, hence a complex notation. First, due to the modulation of the electromagnetic field at the optical frequency of the probe laser, the optical model uses a complex refractive index. Second, the transport model implies the modulation of the pump power. The pump-generated excess carriers and temperature therefore also are written as complex numbers. Obviously, these two complex notations should not be confused or intermixed. Luckily, no ambiguity remains for Si. Indeed, the optical model for PMOR on Si summarized in formulas [9], [11], [14] and [15], is purely real. The only complex notation in the final model will therefore be related to the time variations in the excess carriers and temperature at the modulation frequency of the pump power.

First the excess carrier equations are discussed. The thermodynamic model is an extension of the drift-diffusion model including the thermoelectric effects, i.e. the interactions between temperature and carriers. Here use is made of the model introduced by Kells. The main assumption in this model is that the electrons and holes should be in thermal equilibrium with the lattice (electron temperature $T_n$, hole temperature $T_p$ and lattice temperature T are equal). This assumption is acceptable for silicon if the investigated time scale is not shorter than a few picoseconds, i.e. the thermalization time of hot carriers. Further it is assumed that there is no thermal carrier generation. This can be justified by the low excess temperatures considered here. Also homogeneous Neumann Boundary conditions are assumed. This supposes negligible surface recombinations, which is, in general, not the case. This theory therefore assumes that the studied surfaces are passivated.

The model can be described as follows.

Poisson's equation and the electron and hole continuity equations can be written in their usual form as $$\begin{cases} -\vec{\nabla}\varepsilon_{lattice}\vec{\nabla}\psi = q(P - N + N_d^+ - N_a^-) & [16a] \\ \frac{\partial N}{\partial t} = \frac{1}{q}\vec{\nabla}\cdot\vec{J}_n + G - Rec & [16b] \\ \frac{\partial P}{\partial t} = -\frac{1}{q}\vec{\nabla}\cdot\vec{J}_p + G - Rec & [16c] \end{cases}$$

where ψ is the electrostatic potential, $N=N_{DC}+\Delta N$ and $P=P_{DC}+\Delta P$ are respectively the total electron and hole concentrations, ΔN (resp. ΔP) and $N_{DC}$ (resp. $P_{DC}$) being respectively the modulated electron (resp. hole) concentration and the time-independent electron (resp. hole) concentration. The latter includes the carriers present at equilibrium, the carriers generated by the continuous component of the pump laser, as well as the carriers generated by the probe laser. For the sake of simplicity, $N_{DC}$ and $P_{DC}$ are assumed to be known flat distributions in this investigation. In particular, it is assumed throughout the present theoretical considerations that $N_{DC}=|\Delta N(0,0,0)|$ and $P_{DC}=P_0+|\Delta N(0,0,0)|$, where $P_0$ is the substrate doping concentration. The position (0,0,0) is the origin of a Cartesian coordinate system where the central ray of the pump beam intersects the air-sample interface. This reduces the number of equations to be presented and solved but does not change the physics, which is where the theory is focused on. Rigorously, however, a coupled theory should be presented for the continuous and the modulated excess carriers. $N_d^+$ and $N_a^-$ are respectively the ionized donor and acceptor concentrations. Since one only considers optical generation of excess carriers, the total carrier generation term $G=G[\alpha_{BTB}]$ reads $$G=G[\alpha_{BTB}]=\alpha_{BTB}(1-R_0)P_{pump}\exp(-\alpha_{BTB}z)/(h\nu_{pump}), \qquad [17]$$

$P_{pump}$ being the pump irradiance. Rec is the recombination rate, including both SRH and Auger recombinations. However, TP and CI having high pump irradiances, the carrier-induced recombinations (Auger) are more efficient than the defect-induced recombinations (SRH). This is of course mostly valid in silicon crystals of high purity. One assumes only Auger recombinations. In other words, the total recombination rate $Rec=Rec[C_n,C_p]$ reads $$Rec=Rec[C_n,C_p]=C_nN(NP-n_i^2)+C_pP(NP-n_i^2) \qquad [18]$$

where $C_n$ and $C_p$ are two constants (the possible variation in these constants at ultra high carrier concentrations is not discussed here) and $n_i$ is the intrinsic carrier density. Notice that the equality of the electron and hole recombination rates implicitly assumes negligible trapping. $\vec{J}_n$ and $\vec{J}_p$ are respectively the electron and hole current densities. These currents respectively read $$\begin{cases} \vec{J}_n = \underbrace{-q\mu_nN\vec{\nabla}\psi}_{drift} + \underbrace{qD_n\vec{\nabla}N}_{diffusion} + \underbrace{k_b\mu_nN\vec{\nabla}T}_{Seebeck} - \underbrace{\mu_nN\vec{\nabla}\chi}_{BGN-quasi-drift} & [19a] \\ \vec{J}_p = \underbrace{-q\mu_pP\vec{\nabla}\psi}_{drift} - \underbrace{qD_p\vec{\nabla}P}_{diffusion} - \underbrace{k_b\mu_pP\vec{\nabla}T}_{Seebeck} - \underbrace{\mu_pP\vec{\nabla}(\chi+E_g)}_{BGN-quasi-drift} & [19b] \end{cases}$$

where $\mu_n$ and $\mu_p$ are the electron and hole mobilities respectively. χ is the electron affinity of the considered semiconductor. The electron diffusivity $D_n$ and hole diffusivity $D_p$ are given by the generalized Einstein relation for parabolic bands and Fermi-Dirac statistics $$\begin{cases} D_n = \frac{k_bT}{q}\frac{F_{1/2}\left(\frac{E_{fn}-E_c}{kT}\right)}{F_{-1/2}\left(\frac{E_{fn}-E_c}{kT}\right)}\mu_n & [20a] \\ D_p = \frac{k_bT}{q}\frac{F_{1/2}\left(\frac{E_v-E_{fp}}{kT}\right)}{F_{-1/2}\left(\frac{E_v-E_{fp}}{kT}\right)}\mu_p & [20b] \end{cases}$$

where $k_b$ is Boltzmann's constant. $E_c$ and $E_v$ are respectively the conduction band and the valence band edges. $E_{fn}$ and $E_{fp}$ are respectively the electron and hole quasi-Fermi levels. $F_{1/2}$ and $F_{-1/2}$ are the Fermi integrals.

Both the electron and hole currents proposed in formulas [19] contain four components. First, the usual drift contribution accounts for the movements of charge under an applied electric field (not considered here) and internal electric fields. Two examples of such internal fields are of importance here. The Dember electric field generated by moving distributions of charges with opposite signs is studied here. The built-in electric field of a diode is also discussed here. The second current contribution is the diffusion component, which accounts for the displacement of charges towards regions of low concentration. Third, the thermodynamic model adds a current term proportional to the temperature gradient to embody the Seebeck effect. Finally also the BGN was included quasi-drift currents to account for the drift of electrons under gradients of affinity and the drift of holes under gradients of both affinity and bandgap. It has indeed been shown in the past that the BGN quasi-drift currents are needed to model PMOR correctly. Yet, as already mentioned, local injection of carriers by the pump laser will result in local changes in the band structure. It is shown below that this BGN-induced drift acts as a counter-diffusive term. These third and fourth current contributions are the specificity of our carrier transport model.

Starting from the carrier transport equations [16] combined with the current equations [19], the problem can be simplified to a single equation, namely the generalized ambipolar diffusion equation. To attain this objective, the following four steps are needed.

The first simplification is the charge balance assumption. This assumes that the modulated electron and hole distributions are equal everywhere ($\Delta N=\Delta P$). This assumption has already been used in the optical model. It of course assumes no trapping. It also supposes that electrons and holes diffuse and drift at the same speed.

This can be explained by the internal (Dember) potential which is generated by separated electron and hole distributions. This potential tends to slow down electrons and accelerate holes so as to keep their density equal everywhere. In the isothermal case, this assumption is valid if the Debye length is much smaller than the carrier diffusion length, which is always the case in Si. In the non-isothermal case, one also needs to make sure that the Seebeck currents of electrons and holes do not prevent their ambipolar motion. This assumption is valid if, additionally, $$\frac{\varepsilon_{lattice} k_b}{q^2} \frac{\nabla^2 T}{\Delta N} << 1.$$

Assuming an excess temperature decaying exponentially with a characteristic length $L_{th}$, the above expression becomes $$\frac{L_{Debye}^2}{L_{th}^2} \frac{N}{\Delta N} \frac{\Delta T}{T} << 1$$

which is always the case in Si, in particular in the high carrier injection regime of TP and CI ($<10^{-4}$ even in the worst case of highly doped substrates).

Second, it is assumed that BGN is only due to the generated free carriers. This is clearly the case in a homogeneously doped semiconductor sample. In this case, $\vec{\nabla}\chi=\partial\chi/\partial(\Delta N)\vec{\nabla}(\Delta N)$ and $\vec{\nabla}(\chi+E_g)=\partial(\chi+E_g)/\partial(\Delta N)\vec{\nabla}(\Delta N)$, and the current equations [19] can be rewritten $$\begin{cases} \vec{J}_n = -q\mu_n N\vec{\nabla}\psi + qD_n^{TOT}\vec{\nabla}N + k_b\mu_n N\vec{\nabla}T & [21a] \\ \vec{J}_p = -q\mu_p P\vec{\nabla}\psi - qD_p^{TOT}\vec{\nabla}P - k_b\mu_p P\vec{\nabla}T & [21b] \end{cases}$$

with the total diffusivities $$\begin{cases} D_N^{TOT} = D_n \underbrace{- N\mu_n \frac{\partial\chi}{\partial(\Delta N)}}_{D_n^{BGN}} & [22a] \\ D_p^{TOT} = D_p + P\mu_p \frac{\partial(\chi+E_g)}{\partial(\Delta N)} = D_p \underbrace{- P\mu_p \left|\frac{\partial(\chi+E_g)}{\partial(\Delta N)}\right|}_{D_p^{BGN}}. & [22b] \end{cases}$$

The two derivatives in [22] can be expressed using e.g. Schenk's BGN model. BGN quasi-electric fields act therefore as counter-diffusive terms. The involved additional terms $D_n^{BGN}$ and $D_p^{BGN}$ are indeed always negative, hence reducing the total carrier diffusivities.

Third, the formulas [16b] and [16c] are added respectively multiplied by the hole conductivity $q\mu_p P$ and electron conductivity $q\mu_n N$, using the current formulas [21]. This gives the generalized ambipolar diffusion equation $$\frac{\partial\Delta N}{\partial t} = \underbrace{\frac{\mu_n\mu_p(N-P)}{\mu_n N+\mu_p P}}_{\mu^*}\vec{\nabla}(\Delta N)\cdot\vec{\nabla}\psi + \underbrace{\frac{\mu_p P D_n^{TOT}+\mu_n N D_p^{TOT}}{\mu_n N+\mu_p P}}_{D^*}\nabla^2(\Delta N) + G[\alpha_{BTB}] - Rec[C_n, C_p] + \frac{k_b}{q}\frac{\mu_n\mu_p(N+P)}{\mu_n N+\mu_p P}\vec{\nabla}(\Delta N)\cdot\vec{\nabla}T + \frac{k_b}{q}\frac{2\mu_n\mu_p NP}{\mu_n N+\mu_p P}\nabla^2 T \quad [23]$$

where $\mu^*$ and $D^*$ are respectively the ambipolar mobility and ambipolar diffusivity. Equation [23] contains all the carrier transport information needed for the understanding of a PMOR measurement, not only for silicon but also for any other material where electrothermal ambipolar motion of electrons and holes is allowed.

The fourth and final simplification consists in neglecting three of the terms in formula [23]. First, the drift term is neglected. It was shown indeed that the drift related to the Dember potential is considerably smaller than diffusive effects. Notice that, in addition, at high injection, the ambipolar mobility becomes very small given the involved difference in carrier concentration. Second, the last two (Seebeck) terms of formula [23] are neglected, respectively proportional to the gradient $\vec{\nabla}T$ and laplacian $\nabla^2 T$ of the excess temperature. It is assumed that electrons and holes have equal mobility $\mu$ and equal diffusivity $k_b T\mu/q$. In this case the $\vec{\nabla}T$ term becomes $$\frac{k_b}{q}\frac{\mu_n\mu_p(P+N)}{\mu_n N+\mu_p P}\vec{\nabla}(\Delta N)\cdot\vec{\nabla}T = \frac{k_b}{q}\mu\vec{\nabla}(\Delta N)\cdot\nabla T \quad [24]$$

-continued $$\approx D\vec{\nabla}(\Delta N)\cdot\frac{\vec{\nabla}T}{T}$$

which is smaller than the diffusive term as long as the pump-induced excess temperature is much smaller than room temperature. It is shown below that this is always the case for a silicon substrate in the power range of TP and CI. For other highly absorptive materials like Ge, however, this term may be expected to be significant. Finally, for the $\nabla^2$T term, similar reasoning could be used so as to show that it is usually negligible. However, this conclusion can be reached in a more elegant way. Using the time-independent heat equation, one can show that $$\nabla^2 T = -\frac{(hv_{pump}-E_g)}{k_{th}}G - \frac{E_g}{k_{th}}Rec \quad [25]$$

where $k_{th}$ is the thermal conductivity of the sample. Assuming equal mobility and diffusivity for both types of carriers, it can therefore be deduced that $$\frac{k_b}{q}\frac{2\mu_n\mu_p NP}{\mu_n N+\mu_p P}\nabla^2 T \approx -\frac{2}{1/P+1/N}\left(\underbrace{\frac{D^*(hv_{pump}-E_g)}{k_{th}T}}_{\approx 10^{-21}cm^3}G - \underbrace{\frac{DE_g}{k_{th}T}}_{\approx 10^{-21}cm^3}Rec\right). \quad [26]$$

In other words, this term reduces the carrier generation and enhances the carrier recombinations. In the case of silicon, however, it is smaller than 10% of the carrier recombination and generation rates if the total electron or hole concentration is lower than roughly $10^{20}$ $cm^{-3}$. It is therefore neglected. This term in $\nabla^2$T should, however, be taken into account at very high doping or injection. These results with previously obtained results which confirm that the Seebeck effect is experimentally never observed and therefore negligible compared to the diffusive term and the recombination/generation rates.

As a final remark, the importance of an accurately modeled bandgap is highlighted. Looking at formula [23], there remain indeed only three transport parameters to be correctly accounted for, namely the Auger recombination coefficients ($C_n$ and $C_p$), the band-to-band absorption coefficient ($\alpha_{BTB}$) and the ambipolar diffusivity (D*). First, it is supposed that the Auger coefficients are accurately modeled, even though this is still under discussion in the case of ultra-high doping. Second, Smith's model has been checked to give accurate band-to-band absorption coefficient for undoped Si in a wide range of visible and IR wavelengths. It is however known that this coefficient varies with doping and injection, via BGN. These variations have unfortunately not been verified in literature. Finally, the ambipolar diffusivity also needs to be correctly modeled. Its experimental behavior for lowly doped p- and n-type silicon can be found in literature. It is easy to show that using Klaassen's mobility and formulas [20], a very good agreement is obtained between experiments and theory. However, these experimental data do not involve the BGN counter-diffusive contributions of formulas [22]. The experimental setup used to derive these values induces indeed negligible gradients of carrier concentrations (large beam size and small absorption coefficient). In other words, while it is possible to check the accuracy of the model for ambipolar diffusivity without BGN effects, it is very complex to verify it with BGN effects. Since these effects involve the gradients of the carrier concentrations, this would indeed require monitoring the variations in ambipolar diffusivity with beam size and wavelength. In conclusion, the carrier transport during a PMOR experiment is very sensitive to variations in bandgap with doping and injection. Unfortunately, the existing BGN models still show some discrepancy with experimental data.

As already mentioned, the main assumption concerning the temperatures is the equality of the carrier and lattice temperatures. The heat equation then reads $$\rho c_p\frac{\partial T}{\partial t} = k_{th}\nabla^2 T + G_{th}^{direct} + G_{th}^{recombination} + G_{th}^{Joule} + G_{th}^{Peltier} + G_{th}^{Thomson} \quad [27]$$

where ρ is the density of Si and $c_p$ its heat capacitance.

The first heat generation term is the direct heating (hot-carrier thermalization). This contribution occurs before any carrier transport and reads $$G_{th}^{direct}=G(hv_{pump}-E_g) \quad [28]$$

where empty bands were assumed. This term is not included in Kells's model since Kells considers that the carriers are constantly in thermal equilibrium with the lattice. This is of course not possible in the case of optical generation since the carriers are initially generated with ($hv_{pump}-E_g$) energy in excess to the bandgap. This excess energy is directly (after a few picoseconds) released to the lattice, explaining the presence of this extra term. This term is usually not included in commercial numerical simulation software packages, which makes their use impossible when studying PMOR. For this reason, an own numerical simulation code (FSEM) was written.

Further, the second generation term is the recombination heat $$G_{th}^{recombination}=\text{Rec}(E_{fn}-E_{fp}+qT(P_p-P_n)) \quad [29]$$

where the electron and hole thermoelectric powers assuming Boltzmann statistics are respectively $P_n=-k_b/q\,(5/2\ln(N/N_c))$ and $P_p=k_b/q(5/2-\ln(P/N_v))$. Injecting these formulas into [29] gives $$G_{th}^{recombination}=\text{Rec}(E_g+5kT) \quad [30].$$

Using Boltzmann statistics in the definition of the thermoelectric powers has implicitly modified the impact of band-filling by the excess carriers. As mentioned for the direct heating, empty bands are considered when it comes to heat generation. As the 5kT term of formula [30] is related to band-filling, it has to be ignored. Further, it is observed below that this term needs to be neglected for the sake of energy conservation. This is consistent with the usual modeling.

The next three generation terms are usually not taken into account and are all proportional to a power of the currents. It is easy to show that they all are negligible at room temperature. Using the one-dimensional linear model developed and assuming low-frequency diffusive currents (i.e. $J_n=-J_p=q\sqrt{D/\tau}\Delta N$ where τ is the carrier recombination lifetime) and equal hole and electron mobilities, one finds that $$|G_{th}^{Joule}| = \left|\frac{|\vec{J}_n|^2}{q\mu_n N} + \frac{|\vec{J}_p|^2}{q\mu_p P}\right| \quad [31]$$

$$\leq k_b T\left[\frac{\Delta N}{N} + \frac{\Delta N}{P}\right] Rec$$

$$\leq (2k_b T) Rec$$

$$|G_{th}^{Peltier}| = \left|-T\left[\vec{J}_n \cdot \frac{\partial P_n}{\partial N} \vec{\nabla} N + \vec{J}_p \cdot \frac{\partial P_p}{\partial P} \vec{\nabla} P\right]\right| \quad [32]$$

$$\leq k_b T\left[\frac{\Delta N}{N} + \frac{\Delta N}{P}\right] Rec$$

$$\leq (2k_b T) Rec$$

$$|G_{th}^{Thomson}| = \left|-T\left[\vec{J}_n \cdot \frac{\partial P_n}{\partial T} \vec{\nabla} T + \vec{J}_p \cdot \frac{\partial P_p}{\partial T} \vec{\nabla} T\right]\right| \quad [33]$$

$$\leq \left(k_b \Delta T \left|\ln\left(\frac{NP}{N_c N_v}\right)\right| \sqrt{\frac{D}{2D_{th}}\omega\tau}\right) Rec$$

where $\omega$ is the pump angular modulation frequency. At room temperature, these three heat generation terms account therefore for only a few percent of the recombination heat and can therefore be neglected. It can also be shown that for high-frequency currents, these effects are negligible compared to the transient effects.

It is essential to make sure that the total energy of the system is conserved. The sum of the direct heating and recombination contributions integrated over the sample volume is equal to the incoming optical (non-reflected) energy. In cases where the Joule, Peltier and/or Thomson effects are not negligible, however, ensuring conservation of energy is not as trivial.

To conclude, the transport parameters to be controlled for an optimal modeling of heat transport are discussed. The density, heat capacitance and thermal conductivity of silicon are well known parameters and do not depend on doping or injection (heat conduction through phonons in Si). The only remaining parameters are the band-to-band absorption coefficient and bandgap energy. The accuracy of the model for both parameters have been discussed. In conclusion, the lack of 100% accurate BGN model is clearly one of the drawbacks of this model both for the carrier and the heat transports.

The coupled system of equations to be solved is the following $$\begin{cases} \frac{\partial \Delta N}{\partial t} = \frac{D^* \nabla^2 (\Delta N) + \alpha_{BTB}(1-R_0)P_{pump}(x,y,t)\exp(-\alpha_{BTB}z)}{(h\nu_{pump}) + G^{probe} - Rec[C_n, C_p]} & [34a] \\ \rho c_p \frac{\partial T}{\partial t} = \frac{k_{th} \nabla^2 T + \alpha_{BTB}(1-R_0)P_{pump}(x,y,t)\exp(-\alpha_{BTB}z)(h\nu_{pump} - E_g)}{(h\nu_{pump}) + Rec[C_n, C_p]E_g} & [34b] \end{cases}$$

First the one-dimensional linear solution is discussed. To understand the physics underlying equations [34], the linear problem of a pump laser shining at x=0 on a one-dimensional (lateral) silicon sample is solved. By linear problem, there is meant that the recombination rate is assumed to vary linearly with excess carrier concentration, i.e. Rec=$\Delta N/\tau$ where $\tau$ is the carrier recombination lifetime. The linearity implies also that the ambipolar diffusivity is assumed independent from excess carrier concentration. In particular, $D^*=8$ cm$^2$s$^{-1}$ is considered, which is a typical value for a carrier injection of $10^{18}$ cm$^{-3}$ in a lowly doped Si sample.

The pump irradiance is $P_{pump}\exp(i\omega t)$, i.e. the absorbed photon flux is $J_{absorbed}=J_0\exp(i\omega t)=(1-R_0)P_{pump}/(h\nu_{pump})\exp(i\omega t)$. The pump generates two distributions respectively called the plasma wave $\Delta \tilde{N}(x,t)$ and the thermal wave $\Delta \tilde{T}(x,t)$.

The problem being linear, they both have the same modulation frequency as the pump, i.e. they respectively read $\Delta \tilde{N}(x,t)=\Delta N(x)\exp(i\omega t)$ and $\Delta \tilde{T}(x,t)=\Delta T(x)\exp(i\omega t)$. $\Delta N(x)$ and $\Delta T(x)$ are solutions of the following equations $$\begin{cases} i\omega \Delta N = D^* \frac{\partial^2 \Delta N}{\partial x^2} - \frac{\Delta N}{\tau} & [35a] \\ \rho c_p i\omega \Delta T = k_{th} \frac{\partial^2 \Delta T}{\partial x^2} + E_g \frac{\Delta N}{\tau} & [35b] \end{cases}$$

with respectively the following Neumann boundary conditions at x=0 (under the pump beam)

$$\begin{cases} -D^* \frac{\partial \Delta N}{\partial x}\Big|_{x=0} = J_0 & [36a] \\ -k_{th} \frac{\partial \Delta T}{\partial x}\Big|_{x=0} = J_0(h\nu_{pump} - E_g) & [36b] \end{cases}$$

The two non-homogeneous Neumann boundary conditions respectively contain the information about the pump carrier generation and the direct heat generation. The final solutions of this problem read $$\begin{cases} \Delta N(x) = \frac{J_0}{D^* \sigma_{pl}}\exp(-\sigma_{pl}x) & [37a] \\ \Delta T(x) = \frac{J_0}{k_{th}}\left[\frac{(h\nu_{pump}-E_g)}{\sigma_{th}}\exp(-\sigma_{th}x) + \frac{E_g}{L_{pl}^2(\sigma_{th}^2 - \sigma_{pl}^2)}\left(\frac{1}{\sigma_{pl}}\exp(-\sigma_{pl}x) - \frac{1}{\sigma_{th}}\exp(-\sigma_{th}x)\right)\right] & [37b] \end{cases}$$

where $D_{th}=k_{th}/(\rho c_p)$ is the thermal diffusivity. $\sigma_{pl}=\sqrt{1+i\omega\tau}/L_{pl}$ and $\sigma_{th}=(1+i)/L_{th}$ are respectively the plasma wave and thermal wave vectors, $L_{pl}=\sqrt{D^*\tau}$ and $L_{th}=\sqrt{2D_{th}/\omega}$ being their respective low-frequency diffusion lengths.

All the qualitative physics concerning these damped waves or diffusion wave fields is contained in formulas [37]. FIG. 8 shows the behavior of the amplitudes [resp. $|\Delta N(0)|$ and $|\Delta T(0)|$] and phases [resp. $\phi_{pl}(0)$ and $\phi_{th}(0)$] of these two damped waves under a laser beam for a varying carrier recombination lifetime. It also shows the variations in carrier and thermal diffusion lengths (resp. $L_d^{pl}$ and $L_d^{th}$) and wavelengths (resp. $\lambda_{pl}$ and $\lambda_{th}$). The modulation frequency is 1 MHz, the laser photon energy and irradiance are respectively 1.57 eV and 0.76 MW·cm$^{-2}$. The sample is bare Si, so that $E_g$ is 1.06 eV, $\rho=2.3\times10^{-3}$ kg·cm$^{-3}$, $c_p=700$ J·kg$^{-1}$K$^{-1}$ and $k_{th}=1.3$ W·cm$^{-1}$K$^{-1}$. Two different regimes can be identified on these graphs. First, in the short-lifetime regime, or recombination-limited regime, (corresponding to highly doped or highly injected Si), only the thermal wave shows a wave-like behavior. The plasma wave is a decaying exponential (zero phase and infinite wavelength). Second, in the long-lifetime regime, or diffusion-limited regime, the plasma and thermal waves have very similar wave-like behaviors. The asymptotical behaviors of the presented parameters at short and long lifetimes are also given 8.

For the sake of completeness, notice that the orders of magnitude appearing in FIG. 8 are strongly linked to the one-dimensional character of this example. As shown in the next example, the amplitudes of both the plasma and the thermal waves are strongly reduced in a three-dimensional geometry (about three orders of magnitude less). This can be attributed to the extra two degrees of freedom for diffusion. As for the phase, it is closely related to the type of absorption (surface-restricted or not). It therefore also changes when changing dimensionality. Finally, the diffusion lengths and wavelengths are also reduced in a three-dimensional problem. However, the variations are less than one order of magnitude.

To solve equations (34) on a three-dimensional axisymmetric sample, one either resorts to numerical simulations or to analytical solutions, as developed in the Green function formalism by Mandelis. Comparison of these results in the case of the TP system in the case where BGN is neglected would be advantageous. For the numerical simulations, there is relied on FSEM, a finite-element package developed by the authors. For the analytical solution, the solutions from literature have been implemented. Even though the literature solutions are solutions of the linear equations, the nonlinearity has been included a posteriori in a Newton loop. For this reason, this formulation is called semi-analytical. The only remaining assumption being that the total ambipolar diffusion and the recombination rate have effective uniform values.

The obtained results are shown in FIG. 9 where the amplitudes and phases are plotted at the sample surface (z=0), under the beam (x=y=0), as well as the lateral diffusion lengths and wavelengths of the plasma and thermal waves. The discrepancies between the semi-analytical and numerical formulations can be easily explained by the extra assumption needed to derive the semi-analytical solution. The good overall agreement is, however, an indication that both solutions are valid, i.e. the numerical error is limited in the numerical approach and the assumption used in the analytical solution is acceptable. The values shown in FIG. 9 were obtained by fitting the theoretical results obtained at the sample surface with a typical one-dimensional diffusion-wave field, i.e. a distribution D(x) of the type $$D(x)=D_0\exp(-i\phi)\exp(-x/L)\exp(-2i\pi x/\lambda) \quad [38],$$

where $D_0$ and $\phi$ are respectively the amplitude and phase of the wave under the beam, L and $\lambda$ being respectively its diffusion length and its wavelength.

As highlighted in FIG. 9, four distinct regimes can be identified. First, in region 1 (low doping), a diffusion-limited regime can be observed. This is very interesting since it means that TP is not (or is very weakly) sensitive to recombinations in a lowly doped Si substrate. It is therefore independent from the doping concentration in this region. Second, in regions 2 and 3 (intermediate doping), the recombinations start to impact first the plasma wave (doping >$10^{17}$ $cm^{-3}$) and then the thermal wave (doping >$5\times10^{18}$ $cm^{-3}$). In these two regions, the unexpected behavior of the plasma wave (bump not observed in the one-dimensional solution) can be explained by a fine balance between the increase in recombinations with doping and the simultaneous decrease in ambipolar diffusivity. Finally, in region 4 (high doping), the plasma wave enters a recombination-limited regime. The simplified equations for all four regions are also shown in FIG. 9.

The sensitivity to BGN of these three-dimensional nonlinear plasma and thermal waves is analyzed. The results plotted in FIG. 9 are indeed obtained assuming no BGN. Yet, some coefficients of formulas [34], i.e. $\alpha_{BTB}$, D* and of course $E_g$ itself, do vary with the bandgap energy. The semi-analytical solution for a $10^{15}$ $cm^{-3}$ p-type doping is investigated. In particular, the BGN range included between 0 eV (as above) and $2.0\times\Delta E_g^{Schenk}$ is studied, i.e. twice the BGN value obtained with Schenk's BGN model. It has to be stressed that the whole model, including the derivatives appearing in formulas [22], is scaled by a factor ranging from 0 to 2.0 and plugged into the nonlinear loop. This realistically also accounts for possible quantification errors in Schenk's BGN model. Plasma-induced BGN is considered here. This effect can be accounted for by Schenk's model but has not been experimentally tested, contrary to doping-induced BGN.

The results are shown in FIG. 10. Most important of all, the very strong sensitivity of the plasma wave amplitude is shown in FIG. 10*a*. Compared to the results above, it can be seen that almost one order of magnitude difference can be achieved for a BGN value of $2.0\times\Delta E_g^{Schenk}$. It can easily be shown that the main effect is due to the variation in ambipolar diffusivity. This strong dependence is the result of a positive feedback between the ambipolar diffusivity and the excess carrier concentration. First, the excess carrier concentration increases with decreasing ambipolar diffusivity [see e.g. asymptotical behavior in FIG. 8*a*). Second, $D_n^{BGN}$ and $D_p^{BGN}$ increase with carrier concentration [formulas [22]], hence reducing the ambipolar diffusivity. It is therefore a purely nonlinear effect which explains the strong sensitivity of the plasma wave to BGN. In summary, even a small error on the BGN value is unacceptable for quantitative modeling of PMOR on homogeneously doped Si substrates.

The above transport model is now extended towards doped layers, i.e. the case of actively doped silicon surfaces. It is shown that the excess carrier and temperature profiles can easily be derived from the transport calculations done in the bulk (below the doped surface).

In order to predict the PMOR signals on a doped layer such as described in FIG. 11, one should in theory solve equations [16]. The main difference with the homogeneous case is that an extra electric field has to be taken into account, namely the built-in electric field due to the uncompensated ionized dopant atoms. Indeed, the built-in electric field of active (i.e. annealed) doping profiles modifies strongly the behavior of carriers in the region of the junction and in shallower regions. This obviously invalidates the ambipolar diffusion equation.

However, with the use of four assumptions, it is possible to derive a simplified but complete solution of the carrier and heat transport equations on a sample with an ultra-shallow active doping profile (junction depth $X_j$<100 nm), such as needed in modern CMOS transistors. First, 100% actively doped layers are assumed. Inactive dopants indeed modify the PMOR behavior in a complicated way. Second and third, the heat and carrier generations are assumed independent from the doping profile. This supposes that the penetration depth of the pump laser beam is much longer than $X_j$, which is the case for TP and CI on ultra-shallow junctions (USJs). As a consequence, the heat transport only needs to be solved in the substrate (formula [34b]), neglecting the effect of the layer. As for the carrier transport in the substrate (sub-junction) region, it also has to be solved only once assuming no doped layer (formula [34a]). The fourth and final assumption is the flatness of the electron and hole quasi-Fermi levels through the space-charge region. Quasi-Fermi levels are usually flat in highly conductive regions, whether the free carriers come from doping or optical injection. In order for the currents to flow [$|\vec{J}_i|=|\sigma_i \vec{\nabla} E_{fi}|$ where i=n or p], there is then indeed no need to bend the quasi-Fermi levels. In other words, the semiconductor is considered to have a metallic behavior everywhere. A more comprehensive study of the validity of this assumption has been carried out in literature.

Based on these four assumptions, the transport of optically generated free carriers and heat on USJs can be understood in the following way. First, the heat is generated in the lowly doped substrate, where it diffuses according to formula [34b]. Further, given that doping has a negligible impact on the thermal properties of Si at room temperature, the final excess temperature is layer-independent. Second, similarly, the excess carriers are generated in the substrate where they diffuse ambipolarly and recombine according to formula [34a]. The final excess carrier distribution in the substrate is therefore layer-independent. As for the excess carrier concentration in the layer, it can be estimated by solving Poisson's equation assuming flat quasi-Fermi levels. In other words, there is no carrier transport in the layer. It is the electrostatics which, after carrier transport in the substrate, charges the layer with excess carriers.

In order to determine the excess carrier concentration in the doped layer, one has to solve the electrostatics, i.e. Poisson's equation. However, it is equivalent and much simpler to use the p-n product. The p-n product reads, at each depth z, $$P(z)N(z) = \underbrace{\frac{F_{1/2}((E_v(z)-E_{fp}(z))/(k_bT))}{\exp((E_v(z)-E_{fp}(z))/(k_bT))}}_{\gamma_p}\underbrace{\frac{F_{1/2}((E_{fn}(z)-E_c(z))/(k_bT))}{\exp((E_{fn}(z)-E_c(z))/(k_bT))}}_{\gamma_n} n_i^2\cdot\exp\left(-\frac{E_g(z)}{k_bT}\right)\exp\left(\frac{E_{fn}(z)-E_{fp}(z)}{k_bT}\right). \quad [39]$$

Using formula [39] both in the doped layer and in the substrate offers a simple expression for the excess carrier concentration in the layer. For this purpose, it is assumed here a p-type layer with doping $N_{act}(z)$. First, in the doped layer, the majority hole concentration is $P(z)=N_{act}(z)+\Delta N_l(z)$ and the minority electron concentration is $N(z)=\Delta N_l(z)$. Second, in the highly injected substrate, $N(z)=P(z)=\Delta N_{sub}$. The depth-dependent excess carrier concentration can be obtained using the ratio of formula [39] taken respectively in the layer and in the substrate, i.e.

$$\frac{(N_{act}+\Delta N(z))\Delta N(z)}{\Delta N_{sub}^2} = \frac{\gamma_p^l(z)\gamma_n^l(z)}{\gamma_p^{sub}\gamma_n^{sub}}\exp\left(-\frac{E_g^l(z)-E_g^{sub}}{k_bT}\right) \quad [40]$$

where $\gamma_n^l$ (resp. $\gamma_p^l$) and $\gamma_n^{sub}$ (resp. $\gamma_p^{sub}$) are the electron (resp. hole) Fermi factor as defined above respectively in the layer and in the substrate, $E_g^l$ and $E_g^{sub}$ are respectively the bandgap energies in the layer and in the substrate.

Solving formula (40) for ΔN(z), one obtains $$\Delta N(z) = 0.5\left(-N_{act}(z)+\sqrt{N_{act}^2(z)+4\frac{\gamma_p^l(z)\gamma_n^l(z)}{\gamma_p^{sub}\gamma_n^{sub}}\exp\left(-\frac{E_g^l(z)-E_g^{sub}}{k_bT}\right)\Delta N_{sub}^2}\right). \quad [41]$$

From formula [41], one can show that ΔN(z) decreases with increasing $N_{act}(z)$ in most cases. This explains the monotonically increasing excess carrier profile shown in FIG. 11.

Three additional implicit assumptions have been made in the derivation of formula [41]. First, the Debye length has been assumed much smaller than the characteristic lengths of the profile (junction depth and decay length). The used p-n product supposes a vanishing Debye length, which is valid given the considered high doping concentrations and high injection. Second, in spite of the strong electric field at the junction, the excess electron and hole concentrations have been assumed equal everywhere. This is also related to the very short Debye length. The electric field is only present in a nanometer-wide region around the junction. In that region, the electrons and holes are in slightly different concentrations but this difference is invisible to long wavelengths such as those of the TP or CI probe lasers. Finally, it is also assumed that the substrate excess carrier concentration was flat (see FIG. 11) at the scale of $X_j$. This is related to the penetration depth of the pump and the plasma wave diffusion length being much longer than $X_j$.

It is noticed that since there is no transport in the doped layer, formula [41] is valid at each lateral position. This is of importance for the understanding of PMOR offset curves. Second, formula [41] was derived assuming time-independent behavior of the generated carriers. The generalization to time-dependent excess carriers is not trivial and will be discussed elsewhere. A simplified solution is proposed here, assuming that the excess carriers generated by the continuous and time-dependent components of the pump laser have equal amplitude. Given that the dielectric relaxation time $\tau_d=\epsilon/\sigma$ is of the order of 1 picosecond in Si, the charging of the doped layer with excess carriers occurs much faster than the characteristic time of PMOR (~1/ω) for both TP and CI. The layer charging is therefore considered to be simultaneous with the substrate charging. If one further assumes that $X_j$ is much smaller than the plasma wavelength, the excess carriers in the layer are in phase with those in the substrate. In other words, the amplitude of the modulated excess carrier concentration is calculated using formula [41] and its phase is considered equal to the phase of the modulated excess carriers in the substrate. This insight is necessary in order to understand the behavior of the phase of PMOR signals on active doping profiles. As a final remark, it is pointed out that, in formula [41], BGN plays again a significant role. This shows how crucial a quantitative model for BGN is for the optimal understanding of PMOR signals.

Based on the above model, formulas explaining the PMOR signals which are measured using both the TP and the CI tools are now discussed. The theory is first simplified to the case of box-like active doping profiles. This type of profile is characterized by a uniform active doping $N_{act}$ down to a certain depth $X_j$ below which the doping vanishes. It is shown that the theory can explain the behavior of the signals on such box-like profiles when the doping and/or the junction depth change. For further confirmation of the validity of the model, it then is shown that it is able to explain the behavior of power curves and offset curves.

In a first portion, the theoretical considerations are provided. For a box-like active doping profile, the excess carrier concentration in the layer $\Delta N_l$ is uniform. Combining formulas (9) and (14), one can then show that $$\frac{\Delta R}{R}\bigg|_{box} = \frac{4}{(n_0^2-1)}\cdot\left(-\beta\left(\frac{1}{m_e}+\frac{1}{m_h}\right)\cdot\left(\underbrace{\Delta N_l(1-\cos(4\pi n_0 X_j/\lambda_{probe}))+}_{layer-plasma}\underbrace{\Delta N_{sub}\cos(4\pi n_0 X_j/\lambda_{probe})}_{substrate-plasma}\right)+\underbrace{\delta\Delta T_{surface}}_{thermal}\right) \quad [42]$$

It has here been assumed that the excess temperature is the same in the layer and in the substrate. This is of course only valid for layers much shallower than the thermal diffusion length. The PMOR signal on a box-like active doping profile appears therefore as a three-component signal. The first component is the layer plasma component, related to the excess carrier concentration in the doped layer. This component always has the phase of the plasma component on a homogeneous sample. The second component is the substrate plasma component, linked to the excess carrier concentration in the substrate. Due to the interference between the surface and interface modulated reflections, the sign of this component can change according to the junction depth. Its phase can therefore either be the same as on a homogeneous sample or 180° out of phase. This means that a 180° phase change in a PMOR signal can be attributed not only to a thermal-plasma transition (like on homogeneously doped Si) but also to a substrate-plasma to layer-plasma transition. This occurs, among others, when the pump power is changed, as shown in CI power curves (Section VI.a). The third and final component is the thermal component which is the same as the thermal component on a homogeneous silicon substrate.

The excess carrier concentration in the layer is, following formula [41], $$\Delta N_l = 0.5N_{act}\left(-1+\sqrt{1+4\frac{\Delta N_{sub}^2}{N_{act}^2}}\right) \quad [43]$$

where there is assumed Boltzmann statistics and no BGN. This formula can be further simplified in two cases: (i) when the layer doping is higher than the substrate injection and (ii) when the layer doping is lower than the substrate injection.

(i) $\Delta N_{sub}/N_{act}<1$. In TP and CI, this is the case for active doping concentrations higher than roughly $10^{19}$ $cm^{-3}$. Formula [43] can then be expanded to first order in $\Delta N_{sub}^2/N_{act}^2$, to obtain $$\Delta N_l = \frac{\Delta N_{sub}^2}{N_{act}} \text{ if } \Delta N_{sub}^2/N_{act}^2 << 1. \quad [44]$$

Combining formulas [42] and [44], the final PMOR signal on a box-like active doping profile reads $$\frac{\Delta R}{R}\bigg|_{box} = \frac{4}{(n_0^2-1)}\cdot\left(-\beta\left(\frac{1}{m_e}+\frac{1}{m_h}\right)\left(\underbrace{\frac{|\Delta N_{sub}|^2}{N_{act}}(1-\cos(4\pi n_0 X_j/\lambda_{probe}))+}_{layer-plasma}\underbrace{|\Delta N_{sub}|\cos(4\pi n_0 X_j/\lambda_{probe})}_{substrate-plasma}\right)\exp(-i\varphi_{pl})+\underbrace{\delta|\Delta T_{surface}|\exp(-i\varphi_{th})}_{thermal}\right) \quad [45]$$

This is our final model formula.

The respective phases of the plasma wave $\phi_{pl}$ and of the thermal wave $\phi_{th}$ has been added for the sake of completeness. The equality of the phase $\phi_{pl}$ of the excess carrier concentrations respectively in the substrate and in the layer has here been assumed.

(ii) $\Delta N_{sub}/N_{act}>1$. This corresponds to active doping concentrations lower than approximately $10^{18}$ $cm^{-3}$ in TP and CI. Formula [43] can be expanded to first order in $N_{act}^2/\Delta N_{sub}^2$, which gives $$\Delta N_l^{ld} = \Delta N_{sub} - \frac{N_{act}}{2} \text{ if } N_{act}^2/N_{sub}^2 << 1. \quad [46]$$

The combination of formulas [42] and [46] explains the behavior of PMOR on lowly doped layers.

FIG. 12 shows the experimentally observed PMOR (TP) signals on three sets of samples named respectively CVD2, CVD3 and CVD5. In summary, all three sets are composed of B-doped chemical-vapor deposition (CVD) grown box-like doping profiles with the same doping concentration and different junction depths. The active doping concentrations are respectively ~$2.5\times10^{19}$ $cm^{-3}$ (CVD2), ~$5\times10^{19}$ $cm^{-3}$ (CVD3) and ~$7\times10^{17}$ $cm^{-3}$ (CVD5).

FIG. 12 also shows fitting curves assuming that the substrate plasma component and the thermal component are those obtained on a lowly doped substrate in FIG. 9. The formulas used for fitting are formula [45] for CVD2 and CVD3 and the combination of formulas [42] and [46] for CVD5. The obtained values of $N_{act}$, the only fitting parameter, are about one order of magnitude smaller than the actual active doping concentration. Indeed $9\times10^{17}$ $cm^{-3}$ (CVD2), $1\times10^{18}$ $cm^{-3}$ (CVD3) and $8\times10^{16}$ $cm^{-3}$ (CVD5) was obtained. For reference and to highlight the quantitative disagreement between theory and experiments, the theoretical behavior for $N_{act}=5\times10^{19}$ $cm^{-3}$ is also indicated (dashed cosine of FIG. 12). These discrepancies can be attributed to the assumed Boltzmann statistics as well as the neglected BGN. Notice that the use of Fermi-Dirac statistics with consideration of BGN improves the agreement but is still not satisfactory due to the lack of a quantitative model for BGN (see sensitivity analysis below).

Even though experiments and theory do not agree quantitatively, they clearly do agree qualitatively. First, both the experimental and theoretical curves follow a cosine behavior when the junction depth varies. In particular, the cosine reaches its minimum at $X_j=44$ nm, which is indeed expected for TP ($\lambda_{probe}/(4n_0)=44$ nm). This shows that, as assumed above, the variation in extinction coefficient during a PMOR measurement on silicon is very small (negligible BGN effect on the complex refractive index). Second, for very small $X_j$, all curves converge towards the signal measured on a lowly doped substrate, which confirms the layer-independence of the substrate excess carrier concentration and temperature. Finally, as expected from formula [45], the amplitude of the cosine increases with active doping concentration.

The sensitivity of $\Delta N_l$ to BGN. For simplicity is also analyzed, assuming Boltzmann statistics and $\Delta N_{sub}/N_{act}<1$. Formula [41] then becomes $$\Delta N_l = \frac{\Delta N_{sub}^2}{N_{act}}\exp\left(-\frac{E_g^l - E_g^{sub}}{k_b T}\right) \quad [47]$$

-continued $$= \underbrace{\frac{1}{N_{act}}\Delta N_{sub}^2 \exp\left(\frac{E_g^{sub}}{k_b T}\right)}_{substrate}\underbrace{\exp\left(-\frac{E_g^1}{k_b T}\right)}_{layer}$$

Formula [47] shows that the impact of BGN on $\Delta N_1$ is twofold. The first contribution is a substrate contribution, where BGN affects $\Delta N_1$ indirectly via $\Delta N_{sub}$ (see FIG. 10) and directly via $E_g^{sub}$. The second contribution is a layer contribution, where BGN influences □$N_1$ via the bandgap in the layer $E_g^1$. The effect of BGN is investigated in a similar way as above for homogeneous Si. The BGN range included was studied between 0 eV and $2.0\times\Delta E_g^{Schenk}$. The results are shown in FIG. 13 for a $10^{20}$ $cm^{-3}$ layer doping concentration. A priori, the sensitivity to BGN is even stronger for $\Delta N_1$ than it is for $\Delta N_{sub}$. As indicated by the dotted line, however, the substrate BGN contribution has little impact on $\Delta N_1$. Due to the exponential dependence of formula [47], $\Delta N_1$ can vary over orders of magnitude, but this is due to the layer BGN contribution. Since this contribution is mostly due to active doping (lowly injected layer), i.e. it is doping-induced BGN, it can be assumed that the error on the layer BGN is small. In other words, if the only erroneous BGN contribution is the substrate BGN contribution, this analysis shows that the error made on the layer plasma component is smaller than that made on the substrate plasma component (factor 2 vs. factor 10).

Formula [45] is used to explain CI power curves and TP offset curves. Formula [45] can also predict the behavior of PMOR when the pump power is changed and when the laser beams are separated.

Based on the above PMOR results are now discussed, illustrating features and advantages of one embodiment. CI is a low-frequency PMOR technique with capability of changing the pump power, giving rise to so-called power curves. It assumes that the phase can only be 0° or 180°. In particular, the sign of the CI signal is defined positive if the phase is 180° and negative if the phase is 0°. In other words, using formula [45], the CI signal on a box-like doping profile can be written $$CI = \frac{4G_{CI}}{n_0^2 - 1}\left\{\begin{array}{l}\beta\left(\frac{1}{m_e} + \frac{1}{m_h}\right)\cdot \\ \left(\underbrace{\underbrace{\frac{\Delta N_{sub}^2}{N_{act}}(1-\cos(4\pi n_0 X_j/\lambda_{probe})) +}_{layer-plasma}\underbrace{\Delta N_{sub}\cos(4\pi n_0 X_j/\lambda_{probe})}_{substrate-plasma}}\right) - \underbrace{\delta\Delta T_{surface}}_{thermal}\end{array}\right\} \quad [48]$$

where $G_{CI}$ is the normalization factor of CI signals. This formula is used to explain qualitatively the behavior of the CI signal on CVD2 and CVD3. The measured power curves are shown in FIG. 14.

First the high doping case (CVD3) is discussed. The power curves are almost linear, which shows that the substrate plasma component is dominant. The slope of these power curves is directly related to the junction depth of the measured sample and could therefore be used to determine this junction depth. However, the nonlinearity of equation (34a) as well as the presence of the thermal component could bring some error in the obtained depth values.

In the intermediate doping case (CVD2), the shallow layers show a similar linear behavior (white background). Deeper layers, however, show a strong nonlinear power curve (shaded background). Some of the power curves even change sign, corresponding to a phase transition of the PMOR signal from 180° to 0°. As mentioned above, this is not to be attributed to a plasma-to-thermal transition. This sign change is indeed due to the quadratic behavior of the layer plasma component. At a certain pump power, this positive component becomes larger than the substrate plasma component, which increases linearly with the substrate injection. This transition only occurs if the substrate plasma component is negative. This is only possible for junction depths roughly between $\lambda_{probe}/(8n_0)$ (~34 nm) and $3\lambda_{probe}/(8n_0)$(~102 nm).

To illustrate qualitatively the good agreement between the experimental power curves of FIG. 14 and formula [45], in FIG. 15, the theoretically expected behavior of the PMOR signal as a function of a substrate injection is plotted $DN_{sub}$ in the relevant range included between 0 and $3\times10^{18}$ $cm^{-3}$. For simplicity and in acceptable agreement with literature, it here is assumed that the thermal component accounts for one third of the substrate signal, i.e. $\delta\Delta T=(\beta/3)(1/m_e+1/m_h)\Delta N_{sub}$. It can be seen that formula [45] predicts correctly the overall behavior of the power curves both for medium ($N_{act}=5\times10^{18}$ $cm^{-3}$) and high doping ($N_{act}=1.5\times10^{19}$ $cm^{-3}$). It is to be noticed that the chosen doping concentrations are given here for reference and without any justification (not quantitative due to sensitivity to BGN).

For measured power curves on lowly doped CVD layers (CVD5) shown in literature, it can be seen that the combination of formulas [42] and [46] explains very well the behavior of the power curves. Further it has been shown that carrier profiling of box-like doping profiles could be performed using the inflection point of power curves. Formula [45] shows that the position of this inflection point is mostly linked to the nonlinearity of $\Delta N_{sub}$, and therefore of the ambipolar diffusion equation, i.e. the variations in the recombination rate and ambipolar diffusivity with excess carrier concentration. This explains why this technique has proven difficult to implement in practice.

To prove the good agreement between formula [45] and the observed experimental data, the theoretical and experimental PMOR signals are compared for situations when the laser beams are separated, i.e. the offset curves. It is reminded that TP has the capability of measuring offset curves with a maximum beam separation of 4 m. Unfortunately, while the behavior of power curves is directly given by formula [45], offset curves need some further explanation. As previously mentioned, the PMOR signals on active doping profiles are composed of three components. Yet, these three components do not have the same lateral behavior. First and second, the substrate plasma and thermal components are the easiest to discuss. Since they are assumed to be unaffected by the doped layer, they are just plasma and thermal waves as found in a homogeneous silicon sample. Their lateral behavior is thus as shown in FIG. 9. Third, concerning the layer-plasma component, it is assumed that it also has the form of a diffusion wave (equation [38]) with wavelength $\lambda_1$ and decay length $L_1$. The wavelength should be the same in the layer and in the substrate, since the electrostatics is fast enough to accommodate the excess carrier concentration in the layer with negligible delays. As for its decay length, given that formula [44] must remain valid at any lateral position (no diffusion in the layer), it is required that $$L_l = \frac{L_d^{pl}}{2}. \quad [49]$$

Notice that formula [49] implies that $L_1$ is independent from $N_{act}$. This is due to the sole fact that BGN is neglected and Boltzmann statistics is assumed. The actual (complex) dependence of $L_1$ on active doping is discussed in depth in literature.

An interesting observation is that, for TP, the decay lengths of all three signal components have the same order of magnitude. Indeed, while the substrate plasma diffusion length $L_d^{pl}$~3 μm (FIG. 9), the thermal diffusion length is $L_d^{th}$~2 μm ((FIG. 9 and the layer plasma decay length is $L_l$~1.5 μm. The lateral behavior of TP signals on doped layers should therefore be a subtle mixture of the decays of the three components. On the contrary, if CI offset curves were possible, they would mostly show the decay in the two plasma components, since the thermal diffusion length is much longer due to a low modulation frequency.

The final TP signal as a function of the pump-probe beam separation x reads $$TP(x) = G_{TP}\exp(-i\theta_{TP})\cdot \frac{4}{(n_0^2-1)}\left[ -\beta\left(\frac{1}{m_e}+\frac{1}{m_h}\right) \left( \underbrace{\frac{|\Delta N_{sub}|^2}{N_{act}}(1-\cos(4\pi n_0 X_j/\lambda_{probe}))\exp\left(-\frac{2x}{L_d^{pl}}\right)}_{layer-plasma} + \underbrace{|\Delta N_{sub}|\cos(4\pi n_0 X_j/\lambda_{probe})\exp\left(-\frac{x}{L_d^{pl}}\right)}_{substrate-plasma} \right) \exp(-i\varphi_{pl})\exp\left(-\frac{2i\pi x}{\lambda_{pl}}\right) + \underbrace{\delta|\Delta T_{surface}|\exp\left(\frac{-x}{L_d^{th}}\right)\exp(-i\varphi_{th})\left(\frac{-2i\pi x}{\lambda_{th}}\right)}_{thermal} \right] \quad [50]$$

where $G_{TP}$ and $\theta_{TP}$ are respectively the normalization factor and phase of the TP signals. In the examples discussed here $G_{TP}$=1900 and $\theta_{TP}$=45° is used.

Rigorously, given the finite values of all the involved characteristic lengths, all the formulas derived for PMOR signals, including formula [50], should be integrated over the surface of the probe laser beam. Since here the lateral behavior of the signals is studied, the integration would be even more relevant here but it will be shown that the experimental behavior is well reproduced by formula [50] without these considerations.

By way of illustration, embodiments of the present invention not being limited thereby, experimental results of TP offset curves are discussed below and compared with theoretical behaviors of the TP offset curves. In these experiments, the TP signal itself as a diffusion wave [formula (38)]. Its lateral behavior is therefore fully characterized by the signal decay length $L_d^{signal}$ and signal wavelength $\lambda_{signal}$. In the present example, by definition, $L_d^{signal}$ is the lateral distance needed for the amplitude to drop by a factor exp(1) (i.e. it is linked to the slope of the offset curve of the amplitude) and $\lambda_{signal}$ is the lateral distance needed for the phase to turn 360° (i.e. it is linked to the slope of the offset curve of the phase). Mathematically, following formula [38], this gives $$L_d^{signal} = -\frac{|TP|}{\frac{\partial |TP|}{\partial x}} \quad [51]$$

and $$\lambda_{signal} = -2i\pi\frac{TP/|TP|}{\frac{\partial TP/|TP|}{\partial x}} \quad [52]$$

It is to be noticed that these definitions allow negative values of both the signal decay length and the signal wavelength. One should not be confused by this a priori unphysical possibility, which is just a consequence of the mathematical definitions of these two parameters. Obviously, the decay lengths and wavelengths of the three signal components are always positive. But the PMOR signal is a combination of these three components. Subsequently, the signal amplitude can sometimes increase with laser separation, i.e. the decay length can be negative. Similarly, the signal phase can sometimes decrease with laser separation, i.e. the signal wavelength can be negative. It is shown below that, albeit unexpected, these situations are observed experimentally and can also be explained with the present model.

The experimental data are gathered with the Therma-Probe® (TP) system. Other measurements referred to above are made using a Carrier Illumination™ (CI) systems. TP and CI are two commercial implementations of PMOR. In the present example, TP uses a 670 nm (1.85 eV) probe laser with 2.5 mW power. The pump laser has a 790 nm wavelength (1.57 eV) with 13.5 mW power modulated at 1 MHz. Both laser beams are focused onto a 0.5 μm beam radius. The TP set-up used has the specificity to allow the separation of the two laser beams to up to 4 μm. This enables to study the lateral behavior of the PMOR signal. Separating the beams and recording the PMOR signal behavior as a function of beam separation gives rise to the so-called TP offset curves. On the other hand, CI uses a 980 nm (1.26 eV) probe laser with 2.2 μm beam radius and $8\times10^5$ W·cm$^{-2}$ irradiance. The CI pump laser has 830 nm wavelength (1.49 eV) and a 2 kHz modulation frequency. Its power is focused on a 1.5 μm beam radius and its irradiance can be varied between 0 and $4\times10^5$ W·cm$^{-2}$. The CI system enables therefore to study the injection dependence of the PMOR signal. The so-called CI power curves show the behavior of the PMOR signal as a function of pump power. Since both PMOR implementations use laser in the red and NIR range with high irradiances, the theory here developed focuses mostly on this case.

The experimental and theoretical values of $L_d^{signal}$ and $\lambda_{signal}$ at x=0 are compared. The variations in these two parameters, first, with junction depth and, second, with active doping concentration are discussed. The study of the junction depth dependence is based upon experimental offset curves run on six B-doped layers of the CVD3 matrix [illustrated in FIG. 16 part(a) and FIG. 16 part(b)]. These layers have a common active doping $N_{act}$~$5\times10^{19}$ cm$^{-3}$ and different junction depths. The discussion of the dependence on active doping concentration relies on the offset curves measured on six B-doped layers of the CVD8 matrix [illustrated in FIG. 16 part (c) and FIG. 16 part (d)]. These CVD layers have the same junction depth (~40 nm) and various active doping concentrations.

First the junction depth dependence is considered, i.e. the offset curves measured on the CVD3 matrix [FIG. 16 part (a) and FIG. 16 part (b)]. Due to the high doping in the CVD3 layers, these offset curves show mostly the competition between the substrate plasma and thermal components. Starting with the behavior of the phase at zero beam separation [FIG. 16 part (b)], it can be seen that it varies with junction depth. This is to be attributed to the change in sign of the substrate plasma component when $X_j$=22 nm. The slope of the phase offset curves, and hence the signal wavelength, also changes with junction depth. This variation is due to the different wavelengths of the substrate plasma component and thermal component. On a lowly doped substrate [bold line in FIG. 16 part (b)], the signal wavelength can be calculated to be roughly 130 μm. After a 4 μm distance, the variation in phase is indeed approximately 11°. In other words, a 130 μm distance would be needed to achieve a 360° turn. This is also the wavelength calculated for the plasma wave in a lowly doped substrate [FIG. 12 part (d)]. Such a signal is therefore clearly plasma-dominated. On the contrary, when $X_j$=24 nm, the signal is thermally dominated since it shows a 36 μm wavelength, which is the wavelength of a thermal wave [FIG. 9 part (d)]. Around 22 nm [$=\lambda_{probe}/(8n_0)$], the plasma component indeed vanishes, leaving the thermal component as sole contribution. For other junction depths, the substrate plasma component and the thermal components are in close competition, which explains the varying signal wavelength.

The overall theoretical dependence of the signal wavelength on junction depth is shown in FIG. 17 part (b) in the high doping case, i.e. when the layer-plasma component is absent ($\Delta N_l \approx 0$). In particular, this figure plots the variations in $\lambda_{signal}/\lambda_{signal}$ ($X_j$=0), where $\lambda_{signal}$ ($X_j$=0) is the signal wavelength measured on a lowly doped substrate. The experimental values obtained on the CVD3 matrix are also plotted (circles). It is clear from this figure that the model is able to predict the overall behavior of the signal wavelength quite precisely.

The lateral variation in amplitude of the TP signal on CVD3 shown in FIG. 16 part (a), i.e. the behavior of $L_d^{signal}$, can also look quite peculiar at first sight. Due to the competing behaviors of the substrate-plasma component and the thermal component, the decay length of the TP signal depends on junction depth. The decay length is longer than on a substrate for $X_j$ up to 16 nm. In this case, the substrate plasma component and the thermal component have opposite signs. The dominant plasma wave decays more slowly than the thermal wave, so that the signal decay length is larger. For $X_j$=24 nm and deeper, the signal decay length is shorter than on a substrate. The two signal components having the same sign, the fast decay in thermal component implies a shorter signal decay length.

The theoretical behavior is summarized in FIG. 17 part (a), which plots the $X_j$-dependence of $L_d^{signal}/L_d^{signal}$ ($X_j$=0), where $L_d^{signal}$ ($X_j$=0) is the signal decay length calculated for a lowly doped substrate. The experimental values measured on the CVD3 matrix are also plotted (circles) are close to the predicted values.

Interestingly, FIG. 17 shows that the variations with junction depth in signal decay length and wavelength are complex. It is possible to distinguish three regions. The two lengths can either be longer than on a lowly doped substrate (region 1 of FIG. 17) or shorter (region 2 of FIG. 14), or it can even be negative (region 3 of FIG. 14). The behavior even allows for asymptotes (flat offset curves), corresponding to the roots of the derivatives involved in formulas [51] and [52]. The equations of these asymptotes are quite complicated and are therefore not shown here.

The dependence on active doping of the signal decay length and wavelength for $X_j$=40 nm is now discussed, i.e. the offset curves measured on the CVD8 matrix [FIG. 16 part (c) and FIG. 16 part (d)]. Looking first at the behavior of the phase and the wavelength of the signal [FIG. 16 part (d)], it can be seen that both saturate when a certain active doping concentration is reached (~$5\times10^{19}$ $cm^{-3}$). This can be easily understood if the signal is considered as the competition between the layer plasma and substrate plasma components. Note that these two components have opposite signs [$\lambda_{probe}/(8n_0)<40$ nm$<3\lambda_{probe}/(8n_0)$] and that the layer plasma component decreases with increasing active doping ($\propto 1/N_{act}$). At low doping, the layer plasma component therefore dominates. The change in sign of the phase shows that the layer plasma component decreases. The saturation of the phase and wavelength is then attained when the substrate plasma component fully dominates the layer plasma component.

The behavior of the decay length [FIG. 16 part (c)] also shows the competition between the two plasma components, but in a more complex way. At low doping concentration ($1.1\times10^{19}$ $cm^{-2}$ for this junction depth), the layer plasma component is dominant. The signal decay length is therefore shorter than on a lowly doped substrate (formula [49]). When the doping increases, the substrate plasma component starts to dominate. Very interestingly, at $N_{act}\approx2.5\times10^{19}$ $cm^{-3}$, a negative decay length is observed (lateral increase in signal). This is explained by the fast lateral decay in a layer plasma component slightly dominated by a substrate plasma component with opposite sign. Note that for these lower doped samples, the phase converges to that of the substrate-plasma component as the beam separation increases and the contribution of the layer-plasma component becomes increasingly negligible relative to the substrate-plasma component. For higher doping concentrations, the decay length monotonically decreases. Unlike the wavelength in FIG. 16 part (d), the decay length still shows some sensitivity to active doping concentration even at the highest concentrations (no saturation observed). All these observations are in agreement with the theoretically predicted behavior shown in FIG. 18. FIG. 18 compares the measured values of $L_d^{signal}/L_d^{signal}$ ($X_j$=0) and $\lambda_{signal}/\lambda_{signal}$ ($X_j$=0) to the theory summarized by formulas [50], [51] and [52]. Notice that, due to the absence of a perfectly quantitative model to explain the dependence on $N_{act}$ (due to BGN), two x axes have to be used in FIG. 18. The bottom x axis refers to the experimental values (circles), while the top x axis is used for the theoretical curves.

The dependency of the active doping concentration and the junction depth on the lateral decay length and the wavelength as shown for these examples, illustrates how one embodiment can make use of this correlation for determining the active doping concentration and the junction depth in semiconductor samples.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A method of determining an active dopant concentration profile of a semiconductor substrate based on optical measurements, the active dopant concentration profile comprising a concentration level and a junction depth, the method comprising:

obtaining a photomodulated optical reflectance (PMOR) amplitude offset curve and a PMOR phase offset curve for the semiconductor substrate based on photomodulated reflectance PMOR measurements;

determining a decay length parameter based on a first derivative of the amplitude offset curve with respect to the lateral distance between the locations of the pump and probe beams on the surface of the semiconductor substrate;

determining a wavelength parameter based on a first derivative of the phase offset curve with respect to the lateral distance between the locations of the pump and probe beams on the surface of the semiconductor substrate; and determining with a computer, from the decay length parameter and from the wavelength parameter, the concentration level and the junction depth of the active dopant concentration profile.

2. A method according to claim 1, wherein obtaining a PMOR amplitude offset curve and a PMOR phase offset curve for the semiconductor substrate comprises:

obtaining a semiconductor substrate having an active dopant concentration profile characterized by a concentration level and a junction depth; and optically measuring a PMOR amplitude offset curve and a PMOR phase offset curve for the obtained semiconductor substrate.

3. A method according to claim 1, wherein a first derivative of the amplitude offset curve and a first derivative of the phase offset curve are representative for a change of the obtained PMOR amplitude and phase respectively, with the separation between a point of incidence of a pump laser beam and a probe laser beam used for determining the PMOR amplitude and phase.

4. A method according to claim 1, wherein determining from the decay length parameter and from the wavelength parameter, the concentration level and the junction depth of the active dopant concentration profile comprises:

selecting a predetermined concentration profile shape being function of the concentration level and the junction depth; and determining the concentration level and the junction depth of the active dopant concentration profile based on the combination of the predetermined concentration profile shape and the determined decay length parameter and the wavelength parameter.

5. A method according to claim 4, wherein selecting the predetermined profile shape comprises selecting any of a box-like concentration profile shape or a Gaussian concentration profile shape, a Lorentzian shape, a complementary error function or part thereof.

6. A method according to claim 1, wherein determining from the decay length parameter and from the wavelength parameter, the concentration level and the junction depth of the active dopant concentration profile comprises:

correlating the determined decay length parameter and the determined wavelength parameter with known lateral decay length parameter values and known wavelength parameter values determined for known active dopant profiles; and determining the concentration level and the junction depth from the correlating.

7. A method according to claim 6, wherein the correlating and determining therefrom the concentration level and the junction depth comprises comparing the decay length parameter and the wavelength parameter for the semiconductor substrate with a look up table or a graphical representation of a set of known lateral decay length parameter values and known wavelength parameter values corresponding with known junction depth and peak dopant concentration level.

8. A method according to claim 6, wherein the look up table or graphical representation implements a dataset, the dataset comprising a set of lateral decay length parameter values and wavelength parameter values as function of peak concentration level and a junction depth, each lateral decay length parameter value and wavelength parameter value being based on a first derivative of an amplitude offset curve and a first derivative of a phase offset curve respectively of a photomodulated reflectance measurement of a semiconductor substrate having an active dopant concentration profile having the corresponding peak concentration level and the corresponding junction depth.

9. A method according to claim 6, wherein the known lateral decay length parameter values and the known wavelength parameter values are obtained by optically measuring semiconductor substrates with a known active dopant profile with known junction depth and known peak dopant concentration level.

10. A method according to claim 6, wherein the known lateral decay length parameter values and the known wavelength parameter values are obtained by simulation of semiconductor substrates with a known active dopant profile with known junction depth and known peak dopant concentration level and using a predetermined concentration profile shape.

11. A non-transitory computer-readable medium having stored therein instructions which, when executed on a computer, performs a method comprising:

obtaining a photomodulated optical reflectance (PMOR) amplitude offset curve and a PMOR phase offset curve for the semiconductor substrate based on PMOR measurements;

determining a decay length parameter based on a first derivative of the amplitude offset curve with respect to the lateral distance between the locations of the pump and probe beams on the surface of the semiconductor substrate;

determining a wavelength parameter based on a first derivative of the phase offset curve with respect to the lateral distance between the locations of the pump and probe beams on the surface of the semiconductor substrate; and determining, from the decay length parameter and from the wavelength parameter, the concentration level and the junction depth of the active dopant concentration profile.

12. A computing device for determining an active dopant concentration profile of a semiconductor substrate based on optical measurements, the active dopant concentration profile comprising a concentration level and a junction depth, the computing device comprising:

a processor configured to obtain a photomodulated reflectance (PMOR) amplitude offset curve and a photomodulated reflectance (PMOR) phase offset curve for the semiconductor substrate based on photomodulated reflectance (PMOR) measurements; and the processor further configured to determine a decay length parameter based on a first derivative of the amplitude offset curve with respect to the lateral distance between the locations of the pump and probe beams on the surface of the semiconductor substrate, to determine a wavelength parameter based on a first derivative of the phase offset curve with respect to the lateral distance between the locations of the pump and probe beams on the surface of the semiconductor substrate, and to determine from the decay length parameter and from the wavelength parameter, the concentration level and the junction depth of the active dopant concentration profile.

13. A computing device according to claim 12, wherein the input module is configured to:

obtain a semiconductor substrate having an active dopant concentration profile characterized by a concentration level and a junction depth; and optically measure a PMOR amplitude offset curve and a PMOR phase offset curve for the obtained semiconductor substrate.

14. A computing device according to claim 12, wherein a first derivative of the amplitude offset curve and a first derivative of the phase offset curve are representative for a change of the obtained PMOR amplitude and phase respectively, with the separation between a point of incidence of a pump laser beam and a probe laser beam used for determining the PMOR amplitude and phase.

15. A computing device according to claim 12, wherein the processor is configured to:

select a predetermined concentration profile shape being function of the concentration level and the junction depth; and determine the concentration level and the junction depth of the active dopant concentration profile based on the combination of the predetermined concentration profile shape and the determined decay length parameter and the wavelength parameter.

16. A computing device according to claim 15, wherein the predetermined profile shape is any of a box-like concentration profile shape or a Gaussian concentration profile shape, a Lorentzian shape, a complementary error function or part thereof.

17. A computing device according to claim 12, wherein the processor is configured to:

correlate the determined decay length parameter and the determined wavelength parameter with known lateral decay length parameter values and known wavelength parameter values determined for known active dopant profiles; and determine the concentration level and the junction depth from the correlating.

18. A computing device according to claim 17, wherein the known lateral decay length parameter values and the known wavelength parameter values are obtained by optically measuring semiconductor substrates with a known active dopant profile with known junction depth and known peak dopant concentration level.

19. A computing device according to claim 17, wherein the known lateral decay length parameter values and the known wavelength parameter values are obtained by simulation of semiconductor substrates with a known active dopant profile with known junction depth and known peak dopant concentration level and using a predetermined concentration profile shape.

* * * * *

UNITED STATES PATENT AND TRADEMARK OFFICE

CERTIFICATE OF CORRECTION

PATENT NO. : 8,634,080 B2
APPLICATION NO. : 13/744880
DATED : January 21, 2014
INVENTOR(S) : Janusz Bogdanowicz It is certified that error appears in the above-identified patent and that said Letters Patent is hereby corrected as shown below:

On the Title Page, Item (54) and in the Specification, Column 1, Lines 1-2, change title from "METHOD FOR DETERMINING AN ACTIVE DOPANT CONCENTRATION PROFILE" to -- METHOD FOR DETERMINING AN ACTIVE DOPANT PROFILE --.

In the Specification

In Column 7 at line 36, change "cm$^{-3}$" to -- cm$^{-3}$. --.

Signed and Sealed this
Nineteenth Day of August, 2014

Michelle K. Lee
*Deputy Director of the United States Patent and Trademark Office*